(12) United States Patent
Klauber et al.

(10) Patent No.: US 10,584,102 B2
(45) Date of Patent: Mar. 10, 2020

(54) PROCESS FOR PREPARING 4-AMINO-PYRIDAZINES

(71) Applicant: BASF SE, Ludwigshafen am Rhein (DE)

(72) Inventors: Eric George Klauber, Bad Duerkheim (DE); Michael Rack, Eppelheim (DE); Roland Goetz, Neulussheim (DE); Sebastian Soergel, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/572,303

(22) PCT Filed: May 10, 2016

(86) PCT No.: PCT/EP2016/060461
§ 371 (c)(1),
(2) Date: Nov. 7, 2017

(87) PCT Pub. No.: WO2016/180833
PCT Pub. Date: Nov. 17, 2016

(65) Prior Publication Data
US 2018/0141917 A1    May 24, 2018

Related U.S. Application Data

(60) Provisional application No. 62/159,392, filed on May 11, 2015.

(30) Foreign Application Priority Data

May 26, 2015 (EP) .................................... 15169166

(51) Int. Cl.
| | | |
|---|---|---|
| *C07D 403/12* | (2006.01) | |
| *C07D 237/12* | (2006.01) | |
| *C07D 237/20* | (2006.01) | |
| *C07B 31/00* | (2006.01) | |
| *C07B 39/00* | (2006.01) | |
| *C07B 43/04* | (2006.01) | |

(52) U.S. Cl.
CPC ............ *C07D 237/20* (2013.01); *C07B 31/00* (2013.01); *C07B 39/00* (2013.01); *C07B 43/04* (2013.01); *C07D 237/12* (2013.01); *C07D 403/12* (2013.01)

(58) Field of Classification Search
CPC ... C07D 237/20; C07D 237/12; C07D 403/12
See application file for complete search history.

(56) References Cited

U.S. PATENT DOCUMENTS

| | | | |
|---|---|---|---|
| 4,728,355 A | 3/1988 | Henrie, II | |
| 6,140,332 A * | 10/2000 | Traxler | C07D 207/34 514/252.16 |
| 6,258,822 B1 | 7/2001 | Geyer et al. | |
| 8,987,461 B2 | 3/2015 | Nie et al. | |
| 2010/0305124 A1 | 12/2010 | Fusslein et al. | |
| 2013/0324547 A1 | 12/2013 | Boivin et al. | |
| 2014/0135368 A1* | 5/2014 | Humljan | C07C 41/18 514/376 |
| 2016/0345581 A1 | 12/2016 | Soergel et al. | |
| 2017/0210712 A1 | 7/2017 | Gockel et al. | |

FOREIGN PATENT DOCUMENTS

| | | |
|---|---|---|
| EA | 201270480 A1 | 8/2013 |
| EP | 2671873 A1 | 12/2013 |
| JP | 2007326784 A | 12/2007 |
| WO | 9618628 A1 | 6/1996 |
| WO | 9964402 A1 | 12/1999 |
| WO | 2001007436 A2 | 2/2001 |
| WO | 2002100352 A2 | 12/2002 |
| WO | 2009068652 A1 | 6/2009 |
| WO | 2009027393 A3 | 9/2009 |
| WO | 2009152325 A1 | 12/2009 |
| WO | 2010034737 A1 | 4/2010 |
| WO | 2010049841 A1 | 5/2010 |
| WO | 2010034738 A3 | 10/2010 |
| WO | 2010112177 A1 | 10/2010 |
| WO | 2010142628 A1 | 12/2010 |
| WO | 2011038572 A1 | 4/2011 |
| WO | 2011124524 A1 | 10/2011 |
| WO | 2012019015 A2 | 2/2012 |
| WO | 2012098387 A1 | 7/2012 |
| WO | 2012142217 A1 | 10/2012 |
| WO | 2012143317 A1 | 10/2012 |

(Continued)

OTHER PUBLICATIONS

International Search Report and Written Opinion for International Application No. PCT/EP2016/060461, dated May 10, 2016.
Tsukasa Kuraishi et al: "Synthesis of 4-Aminopyridazine", Pharmaceutical Bulletin, vol. 4, No. 2, Jan. 1, 1956, pp. 137-138.
Fei Chang et al: "Pd-catalyzed Dehalogenation of Aromatic Halides Under Solvent-free Conditions Using Hydrogen Balloon", Bulletin of the Korean Chemical Society, vol. 32, No. 3, Mar. 20, 2011, pp. 1074-1076.
Peet, Journal of Heterocyclic Chemistry 21(5), 1984, pp. 1389-1392.

(Continued)

*Primary Examiner* — Emily A Bernhardt
(74) *Attorney, Agent, or Firm* — Brinks Gilson & Lione

(57) ABSTRACT

Provided herein is a process for preparing a pyridazine amine compound of formula V, and a process for preparing dichloropyridazine amine compounds of formula IVa, IVb, and mixtures thereof. Further, provided herein are novel dichloropyridazine amine compounds of formula IVa, IVb, and mixtures thereof, wherein the amino group is an ethylamino group.

11 Claims, No Drawings

(56) References Cited

FOREIGN PATENT DOCUMENTS

| WO | 2013004984 A1 | 1/2013 |
|---|---|---|
| WO | 2013142269 A1 | 9/2013 |
| WO | 2013189801 A1 | 12/2013 |
| WO | 2014091368 A1 | 6/2014 |
| WO | 2015162133 A1 | 10/2015 |
| WO | 2015169734 A1 | 11/2015 |
| WO | 2015189080 A1 | 12/2015 |
| WO | 2016016369 A1 | 2/2016 |
| WO | 2016128239 A1 | 8/2016 |
| WO | 2016128240 A1 | 8/2016 |
| WO | 2016128261 A2 | 8/2016 |
| WO | 2017133942 A1 | 8/2017 |

OTHER PUBLICATIONS

Botteghi, et al. Journal of Organometallic Chemistry, 1989, 370, pp. 17-31. English Abstract.

Baranov, et al. Russian Journal of Applied Chemistry, vol. 77, No. 12, 2004, pp. 1997-2000.

Romero et al. "Targeting Delavirdine/Atevirdine Resistant HIV-1: Identification of (Alkylamino)piperidine-Containing Bis(heteroaryl)piperazines as Broad Spectrum HIV-1 Reverse Transcriptase Inhibitors," J. Med. Chem, 1996, 39, 3769-3789.

Alemagna, A., et al., "Arylazomethylenetriphenylphosphoranes: intra molecular reactions with aldonitronyl substituents in the ortho position with respect to the azophosphorane group", Tetrahedron, vol. 41, No. 12, Jan. 1, 1985, pp. 2503-2511.

Altenbach, et al., "Synthesis, Potency, and In Vivo Profiles of Quinoline Containing Histamine H3 Receptor Inverse Agonists", Journal of Medicinal Chemistry, vol. 50, Issue 22, 2007, pp. 5439-5448.

Holschbach, MH et al., "Synthesis of 2-benzyl-2H-pyrazole-3, 4-diamine dihydrochloride," Tetrahedron Letters, Pergamon, GB, vol. 44, No. 1, Jan. 1, 2003, pp. 41-43.

Konyukhova, N.A. et al., "Chemistry of Heterocyclic Compounds," vol. 37, No. 6, Jan. 1, 2001, pp. 779-780.

Kralj, D et al., "3-(Dimethylamino) Propenoate-Based Regioselective Synthesis of 1, 4-Dusibstituted 5-Hydroxy-1-Hpyrazoles," Heterocycles: An International Journal For Review and Communications in Heterocyclic Chemistry, Japan Institute of Heterocyclic Chemistry, JP, vol. 68, No. 5, Mar. 31, 2006, pp. 897-914.

Lipunova, G N et al., "Fluorine-Containing Heterocycles: VIII. Transformations of 2-Polyfluorobenzoylacrylates Having a Thiosemicarbazide Fragment," Russian Journal of Organic Chemistry, Consultants Bureau, US, vol. 38, No. 12, Dec. 1, 2002, pp. 1851-1856.

Weigert, et al.,"Hexafluoracetone hydrazone chemistry," Journal of Flourine Chemistry, Elsevier NL, vol. 1, No. 4, Apr. 1, 1972, pp. 445-462.

Yakimovich, S.I. et al., "Reactions of 3-ethoxymethylidenipentane-2, 4-dione and ethyl 2-ethoxymethylidene-3, oxobutanoate with benzohydrazide," Russian Journal of Organic Chemistry, vol. 44, No. 4, Apr. 1, 2008, pp. 621-623.

* cited by examiner

PROCESS FOR PREPARING 4-AMINO-PYRIDAZINES

CROSS-REFERENCE TO RELATED APPLICATIONS

This application is the national stage entry of PCT/EP2016/060461 filed on May 10, 2016, which claims the benefit of priority to U.S. Provisional Patent Application No. 62/159,392, filed on May 11, 2015, and to European Patent Application No. 15169166.4, filed on May 26, 2015, which are incorporated by reference in their entirety herein.

FIELD OF DISCLOSURE

The present invention relates to a process for preparing a pyridazine amine compound of formula V according to the following reaction sequence:

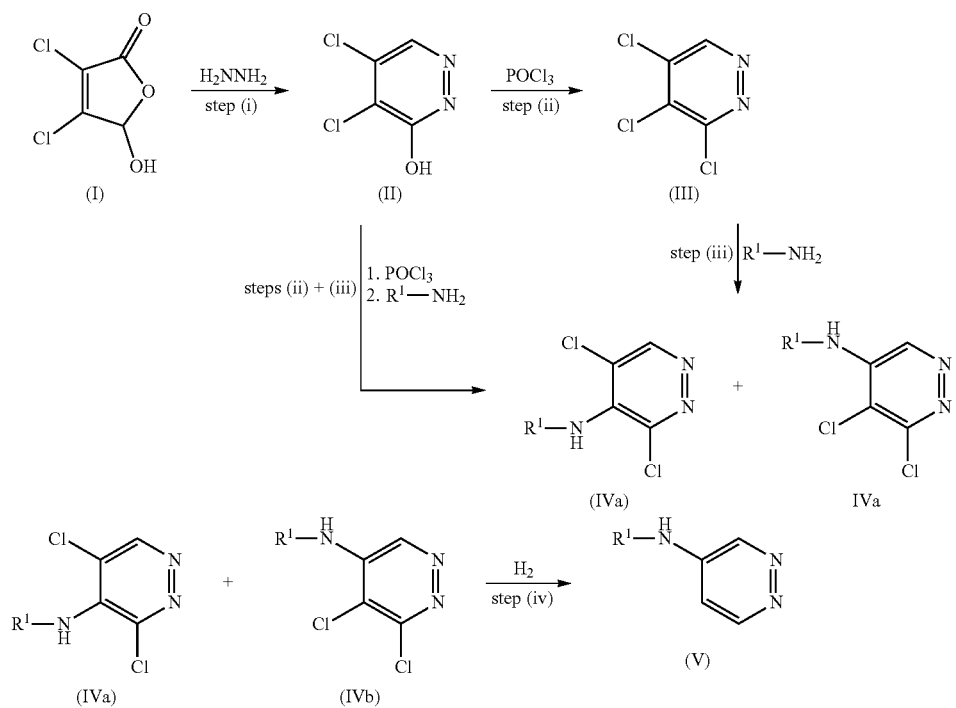

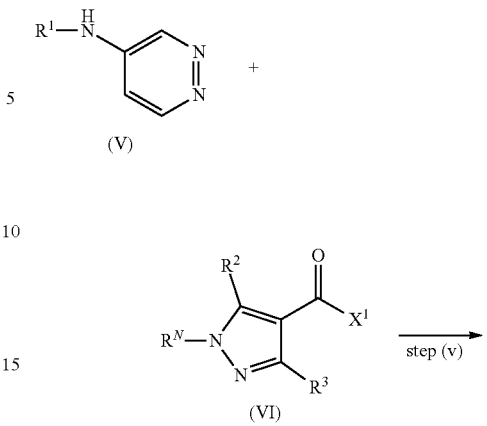

In the above scheme and in the following, step (i) represents the conversion of mucochloric acid I into a compound of formula II, step (ii) represents the conversion of a compound of formula II into the trichloropyridazine compound of formula III, step (iii) represents the conversion of the trichloropyridazine compound of formula III into a mixture of the dichloropyridazine amine compounds of formula IVa and IVb, and step (iv) represents the conversion of the mixture of the compounds of formula IVa and IVb into the pyridazine compound of formula V. It is emphasized that steps (ii) and (iii) may also be accomplished by a one-pot reaction, which is indicated by referring to steps (ii)+(iii) in the above scheme.

The obtained pyridazine amine compounds of formula V may be reacted with compounds of formula VI to give compounds of formula VII according to the following reaction scheme, -continued

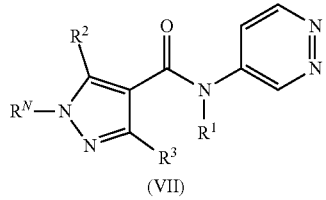

It is in the following referred to this reaction step as step (v).

BACKGROUND

Pyridazine amine compounds, in particular pyridazine amine compounds with an amino group in the 4-position of the pyridazine moiety, are versatile intermediate compounds for the preparation of pyridazine derived fine chemicals, such as compounds in the pharmaceutical and agrochemical field. For example, pyridazine amine compounds are in the focus of research for pharmaceuticals, which are e.g. suitable for the treatment of Alzheimer dementia, depression, hypotension, and anxiety. Furthermore, pyridazine amine compounds are versatile intermediate compounds for the preparation of pesticides with a pyridazine moiety, such as 4-pyrazole-N-pyridazineamide compounds, which are known to be particularly useful for combating invertebrate pests (see WO 2009/027393, WO 2010/034737, WO 2010/034738, and WO 2010/112177).

For certain applications, pyridazine amine compounds are desired, which do not comprise any further substituents apart from the amino substituent, especially pyridazine amine compounds, which are not further substituted by halogen substituents, e.g. chlorine. However, chlorine substituents are often present in pyridazine amine compounds, as the typical starting material for the preparation of these compounds by means of a nucleophilic substitution reaction with an amine compound is 3,4,5-trichloropyridazine.

In view of the above, there is a need for an effective dehalogenation process, by which dichloropyridazine amine compounds can be converted into pyridazine amine compounds. In particular, there is a need for a process, which provides improved yields. In view of subsequent transformations of the resulting pyridazine amines, it is further desired to perform the reaction without the addition of water.

It is known in the art that dehalogenation of certain dichloropyridazine amine compounds can be performed by a hydrogenation/dehalogenation reaction in the presence of hydrogen and a hydrogenation catalyst. The art suggests that this hydrogenation/dehalogenation of pyridazine amine compounds is performed in the presence of a base. In this regard, reference is made to WO 2011/038572; Journal of Heterocyclic Chemistry, 21(5), 1389-92; 1984; WO 2009/152325; U.S. Pat. No. 4,728,355; WO 2011/124524; WO 2010/049841; WO 2013/142269; U.S. Pat. No. 6,258,822; and WO 2001/007436. For example, WO 2011/038572 discloses the dehalogenation of a mixture of 3,5-dichloro-4-pyridazineamine and 5,6-dichloro-4-pyridazineamine by reacting the mixture with hydrogen in the presence of a hydrogenation catalyst (Pd/C) and a base (sodium hydroxide).

The reason why the base is added is to avoid catalyst poisoning due to the production of HCl in the reaction. This is explained by F. Chang et al. in Bull. Korean Chem. Soc. 2011, 32(3), 1075, an article that relates to Pd-catalyzed dehalogenations of aromatic halides. It is disclosed that HCl produced from dechlorination tends to be absorbed on the activated carbon, leading to a progressive poisoning of Pd/C, and that it is efficient to add some bases for the removal of HCl. It is further disclosed that the conversions in the dechlorination reaction can be increased in the presence of a base.

However, the addition of a base is disadvantageous, in particular for an industrially applicable process. First, an additional chemical substance is required for the reaction, i.e. the base, which makes the process more complex. Second, the presence of the base makes catalyst recycling difficult. In particular, when filtering off the hydrogenation catalyst after the reaction, chloride salts obtained from the reaction of the base with the HCl will additionally be filtered off, so that the filter cake comprises both, the catalyst and the chloride salt (e.g. KCl and KHCO$_3$). A further work-up procedure is then required to isolate the catalyst again.

DESCRIPTION

It is therefore an object of the present invention to provide a process for the dehalogenation of dichloropyridazine amine compounds, which is suitable for industrial application.

In particular, it is an object of the present invention to provide a process, which does not require the addition of a base as a further chemical substance, and which provides the advantage that the hydrogenation catalyst may be recycled after the reaction without purification. At the same time, it is of course desired to provide high yields of the process.

The above object is achieved by the process A as described hereinafter and in independent claim 1 and the claims directly or indirectly depending thereon.

In a first aspect, the present invention therefore relates to a process, which is in the following referred to as process A, for preparing a pyridazine amine compound of formula V or a salt, tautomer, or N-oxide thereof

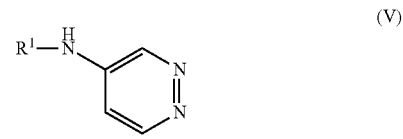

comprising the step of reacting (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b)

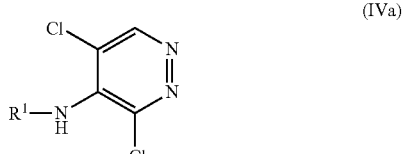

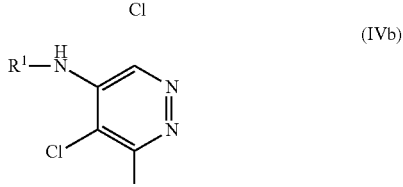

with hydrogen in the presence of a hydrogenation catalyst,
wherein
$R^1$ is H, $C_1$-$C_2$-alkyl, or $C_1$-$C_2$-alkoxy-$C_1$-$C_2$-alkyl.

It is noted that the reaction step underlying process A corresponds to step (iv) in the above reaction sequence.

It has surprisingly been found by the inventors of the present invention that the dehalogenation of dichloropyridazine amine compounds can be performed in the absence of a HCl scavenger, i.e. in the absence of a base or another chemical substance suitable for binding HCl, and that the desired product can nevertheless be obtained in high yields. The hydrogenation catalyst may simply be filtered off after the reaction and can be recycled without purification.

It has further been found that a HCl scavenger may advantageously be used after removal of the hydrogenation catalyst, so that the hydrogen chloride is bound and will not be set free in gaseous form.

When a HCl scavenger is used after removal of the hydrogenation catalyst, it has been found that it is advantageous, if the HCl scavenger is provided without water, because this facilitates the work-up.

Furthermore, it has surprisingly been found by the inventors of the present invention that the yields of the dehalogenation of dichloropyridazine amine compounds depend on the nature of the amino substituent. In this connection, it has surprisingly been found that the reaction may advantageously be carried out with dichloropyridazine amine compounds, wherein the amino group is an ethylamino group.

Also dichloropyridazine amine compounds are versatile intermediate compounds for the preparation of pyridazine derived fine chemicals, such as compounds in the pharmaceutical and agrochemical field. In particular, the chlorine substituents allow for further derivatizations of the pyridazine moiety, e.g., the introduction of additional amino groups by means of a nucleophilic substitution reaction. Accordingly, a broad variety of compounds is available from dichloropyridazine amine compounds, as not only the amine group may be reacted, e.g. with an activated carboxylic acid derivative, but also the chlorine substituents may be replaced by other substituents.

Accordingly, there is also a need for an effective process for the preparation of dichloropyridazine amine compounds.

Furthermore, there is a need for the provision of dichloropyridazine amine compounds, wherein the amino group is an ethylamino group, as these compounds or mixtures thereof are of particular interest as intermediates in the preparation of pesticides and pharmaceuticals.

Typically, dichloropyridazine amine compounds are prepared starting from 3,4,5-trichloropyridazine by means of a nucleophilic substitution reaction with an amine compound.

For example, WO 2011/038572 describes the preparation of a mixture of 3,5-dichloro-4-pyridazineamine and 5,6-dichloro-4-pyridazineamine by reacting 3,4,5-trichloropyridazine with ammonia gas for a reaction time of 4 days. The same reaction is also described in U.S. Pat. No. 4,728,355, wherein the reaction is performed in a sealed tube at a temperature of 120-130° C. for five days. The reaction is performed at 125° C. for 5 hours, according to Tsukasa Kuraishi et al. (Journal of Heterocyclic Chemistry, 1964, Vol. 1, pp. 42-47).

The above described reaction conditions for this reaction already indicate that the art suggests that either long reaction times or high temperatures are required for the nucleophilic substitution reaction, both being disadvantageous for commercial processes.

Furthermore, the preparation of dichloropyridazine amine compounds by reacting 3,4,5-trichloropyridazine with an amine compound, which is different from ammonia, seems to be accompanied by further problems.

WO 99/64402 discloses the reaction of 3,4,5-trichloropyridazine with 3-amino-1-propanol as nucleophile. Although the reaction is performed in boiling ethanol, the yields are very low (only 47.7% of the crude product), and a laborious work-up by means of crystallization is required to isolate the desired reaction products.

WO 2012/098387 discloses the reaction of 3,4,5-trichloropyridazine with 2-methylaminoethanol as nucleophile. Although a secondary amine, which is more nucleophilic than a primary amine is used as a nucleophile, the reaction is not quantitative, and a laborious work-up by column chromatography is required.

Donna L. Romero et al. (Journal of Medicinal Chemistry, 1996, Vol. 39, No. 19, pp. 3769-3789) disclose the reaction of 3,4,5-trichloropyridazine with isopropylamine as a nucleophile. According to the information provided in the article, the reaction has to be performed in refluxing toluene, i.e. at a temperature of about 110° C. Furthermore, chromatography is required for purification.

Similarly, WO 96/18628 discloses the same reaction, wherein 3,4,5-trichloropyridazine and isopropylamine are refluxed in toluene for three hours. Column chromatography is required afterwards to isolate the desired compound 4-isopropylamino-3,5-dichloropyridazine.

Thus, the processes for the preparation of dichloropyridazine amines as described in the prior art are either disadvantageous in terms of the reaction conditions, the yields, and/or the work-up requirements.

Furthermore, it is another disadvantage of the processes described in the art that the irritant compound 3,4,5-trichloropyridazine has to be prepared and handled as a starting material. Solid handling of 3,4,5-trichloropyridazine is particularly disadvantageous on commercial scale.

It is therefore an object of the present invention to provide a process for the preparation of dichloropyridazine amine compounds, which overcomes the disadvantages in terms of the reaction conditions, the yields, and/or the work-up requirements as evident from the prior art, or the disadvantage in terms of the use of the irritant 3,4,5-trichloropyridazine as a starting material.

In this connection, it is of particular interest to provide a straightforward process, which is suitable for upscaling and provides satisfying yields, preferably yields of more than 90%.

The above object is achieved by the process B as described hereinafter.

In a second aspect, the present invention therefore relates to a process, which is in the following referred to as process B, for preparing (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b)

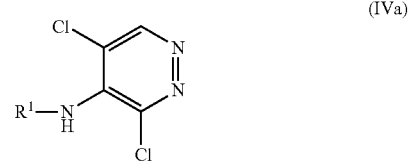

(IVa)

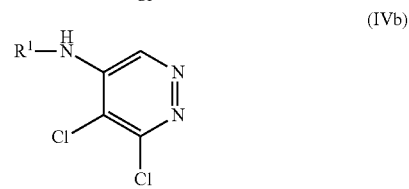

(IVb)

in a one-pot reaction comprising the steps of reacting a compound of formula II

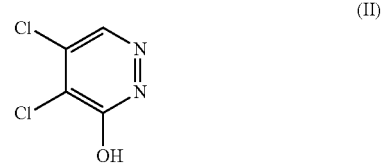

(II)

with POCl₃, and
reacting the resulting crude reaction product with an amine compound R¹—NH₂ or a salt thereof, wherein R¹ is H, C₁-C₂-alkyl, or C₁-C₂-alkoxy-C₁-C₂-alkyl.

It is noted that the one-pot reaction underlying process B corresponds to steps (ii)+(iii) in the above reaction sequence.

It has surprisingly been found that the process of preparing dichloropyridazine amine compounds does not necessarily have to be started from 3,4,5-trichloropyridazine. Instead, 3,4,5-trichloropyridazine may be prepared in situ in a one-pot reaction with a compound of formula II as starting material. The in situ formed 3,4,5-trichloropyridazine is then directly reacted with the amine compound to give the desired dichloropyridazine amine compounds.

This process is particularly advantageous for safety reasons, as it is not required to isolate and handle the irritant compound 3,4,5-trichloropyridazine. This makes the process more favourable for industrial applications. Furthermore, the process is more economic and is suitable for upscaling.

In addition, it has been found that very high yields of the dichloropyridazine amine compounds can be obtained by the above process, whereby the reaction of the in situ formed 3,4,5-trichloropyridazine with the amine compound does not require harsh reaction conditions. Due to the high yields, a laborious work-up can also be avoided.

The above object is also achieved by the process C as described hereinafter.

In a third aspect, the present invention therefore relates to a process, which is in the following referred to as process C, for preparing (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b)

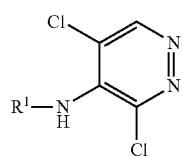
(IVa)

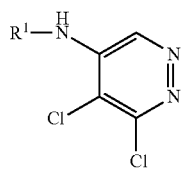
(IVb)

comprising the step of reacting a trichloropyridazine compound of formula III

(III)

with an amine compound R¹—NH₂ or a salt thereof,
wherein R¹ is CH₂CH₃,
and wherein the process optionally further comprises the step of preparing the trichloropyridazine compound of formula III

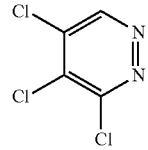
(III)

by reacting a compound of formula II

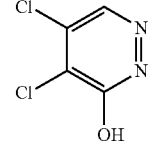
(II)

with POCl₃.

It is noted that the reaction step underlying process C is covered by step (iii) in the above reaction sequence. Optionally, step (ii) of the above reaction sequence is also performed.

It has surprisingly been found that the process of preparing dichloropyridazine amine compounds is particularly advantageous if ethylamine is used as a nucleophile in the nucleophilic substitution reaction. Although the prior art suggests harsh reaction conditions or at least very long reaction times for the nucleophilic substitution reaction, it has been found by the inventors of the present invention that moderate reaction conditions with reaction temperatures of, e.g., not more than 100° C. and reaction times of not more than 12 hours suffice to provide the desired dichloropyridazine ethylamines with high yields, and without having to perform a laborious work-up.

In a fourth aspect, the present invention relates to the dichloropyridazine amine compound of formula IVa or a salt, tautomer, or N-oxide thereof;

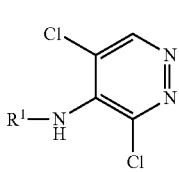
(IVa)

wherein R¹ is CH₂CH₃;
or a dichloropyridazine amine compound of formula IVb or a salt, tautomer, or N-oxide thereof,

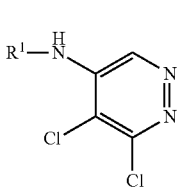
(IVb)

wherein R¹ is CH₂CH₃.

Furthermore, the present invention relates to a mixture of the dichloropyridazine amine compound of formula IVa or a salt, tautomer, or N-oxide thereof and the dichloropyridazine amine compound of formula IVb or a salt, tautomer, or N-oxide thereof as defined above.

As already indicated above, these compounds are highly versatile precursors for the preparation of chemicals, such as compounds in the pharmaceutical and agrochemical field. They may also advantageously be used in the hydrogenation/dehalogenation process as described herein.

In a fifth aspect, the present invention relates to a process for the preparation of a compound of formula VII* or a stereoisomer, salt, tautomer, or N-oxide thereof

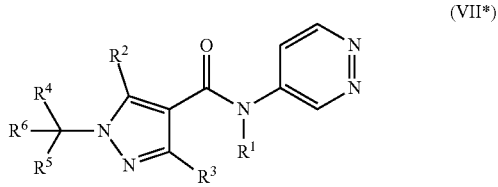

(VII*)

comprising the step of reacting a pyridazine amine compound of formula V or a salt, tautomer, or N-oxide thereof

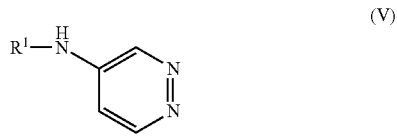

(V)

with a compound of formula VI* or a stereoisomer, salt, tautomer, or N-oxide thereof

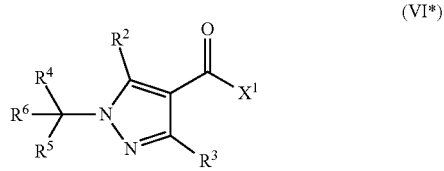

(VI*)

wherein
$R^1$ is $CH_2CH_3$; and wherein
$R^2$ is $CH_3$, $R_3$ is H, $R^4$ is $CH_3$, $R^5$ is $CH_3$ and $R^6$ is H; or
$R^2$ is $CH_3$, $R_3$ is H, $R^4$ is $CF_3$, $R^5$ is $CH_3$ and $R^6$ is H; or
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is $1\text{-}CN\text{-}cC_3H_4$, $R^5$ is $CH_3$ and $R^6$ is H; or
$R^2$ is $CH_3$, $R_3$ is H, $R^4$ is $1\text{-}C(O)NH_2\text{-}cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H;
and wherein
$X^1$ is a leaving group, which is preferably selected from halogen, $N_3$, p-nitrophenoxy, and pentafluorophenoxy, and is particularly preferably chlorine.

Said process is in the following referred to as process D. It is noted that the reaction step underlying process D is covered by step (v) in the above reaction sequence.

The process illustrates that the pyridazine amine compounds, which can be obtained by the hydrogenation/dehalogenation process as described herein are important intermediates in the preparation of 4-pyrazole-N-pyridazineamide compounds, which are pesticides, e.g., suitable for controlling invertebrate pests.

It is to be understood that processes A, B, C, and D as defined above may optionally further comprise additional reaction steps of the reaction sequence provided above.

For example, process A may optionally further comprise step (iii) and optionally also step (ii), wherein steps (ii) and (iii) may be carried out separately or together as steps (ii)+(iii) in a one-pot reaction. In addition, process A may optionally further comprise step (i). Furthermore, it is to be understood that process A may optionally further comprise step (v).

Process B may optionally further comprise step (i) and/or step (iv). In addition, step (v) may optionally follow after step (iv).

Process C may optionally further comprise step (i) and/or step (iv). In addition, step (v) may optionally follow after step (iv).

Process D may optionally further comprise one or more of the preceding steps (iv), (iii), (ii), or (i) as indicated in the above reaction sequence.

It is to be understood that the reaction steps of the above indicated reaction sequences, which are preferably covered by processes A, B, C, or D, may be carried out separately, i.e. under isolation of the intermediate compounds, or without isolating the intermediate compounds. In particular, it is preferred that certain subsequent steps are performed in one-pot reactions as e.g. in case of steps (ii)+(iii).

Furthermore, it is emphasized that the reaction steps may each be performed on a technical scale. Preferably, the reactants are converted equally well and only minor deviations in terms of the yield are observed.

In connection with the above aspects of the present invention, the following definitions are provided.

The "compounds of the present invention" or "compounds according to the invention", i.e. the compounds of formulae I, II, III, IVa, IVb, V, VI, and VII (as well as VI* and VII*) as defined herein, comprise the compound(s) as such as well as salts, tautomers or N-oxides thereof, if the formation of these derivatives is possible; and, if centres of chirality are present, which may particularly be the case for compounds VI and VII as well as compounds VI* and VII*, also stereoisomers thereof.

As used herein, the term "pyridazine amine compound(s)" refers to compounds of formula V, i.e. pyridazine compounds with an amino group —$NHR^1$ as substituent in the 4-position of the pyridazine moiety. Thus, pyridazine amine compounds according to the invention do not comprise any further substituents at the pyridazine ring.

As used herein, the term "dichloropyridazine amine compound(s)" covers compounds of formula IVa or IVb or the combination thereof, i.e. pyridazine compounds with an amino group —$NHR^1$ as substituent and two chlorine substituents, wherein the substituents are present at those positions of the pyridazine moiety, which can be derived from formula IVa and IVb.

As used herein, the term "trichloropyridazine amine compound(s)" preferably refers to compounds of formula III, i.e. 3,4,5-trichloropyridazine.

Depending on the acidity or basicity as well as the reaction conditions, the compounds of the present invention may be present in the form of salts. Such salts will typically be obtained by reacting the compound with an acid, if the compound has a basic functionality such as an amine, or by reacting the compounds with a base, if the compound has an acidic functionality such as a carboxylic acid group.

Cations, which stem from a base, with which the compounds of the present invention are reacted, are e.g. alkali metal cations $M_a^+$, alkaline earth metal cations $M_{ea}^{2+}$ or ammonium cations $NR_4^+$, wherein the alkali metals are preferably sodium, potassium or lithium and the alkaline earth metal cations are preferably magnesium or calcium, and wherein the substituents R of the ammonium cation $NR_4^+$ are preferably independently selected from H, $C_1$-$C_{10}$-alkyl, phenyl and phenyl-$C_1$-$C_2$-alkyl. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzylt-rimethylammonium and benzl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions, which stem from an acid, with which the compounds of the present invention have been reacted, are e.g. chloride, bromide, fluoride, hydrogensulfate, sulfate, dihydrogenphosphate, hydrogenphosphate, phosphate, nitrate, bicarbonate, carbonate, hexafluorosilicate, hexafluorophosphate, benzoate, and the anions of $C_1$-$C_4$-alkanoic acids, preferably formate, acetate, propionate and butyrate.

Tautomers of the compounds of the present invention include keto-enol tautomers, imine-enamine tautomers, amide-imidic acid tautomers and the like. The compounds of the present invention cover every possible tautomer.

The term "N-oxide" relates to a form of the compounds of the present invention in which at least one nitrogen atom is present in oxidized form (as NO). N-oxides of the compounds of the present invention can only be obtained, if the compounds contain a nitrogen atom, which may be oxidized. N-oxides may principally be prepared by standard methods, e.g. by the method described in Journal of Organometallic Chemistry 1989, 370, 17-31. However, it is preferred according to the invention that the compounds are not present in the form of N-oxides. On the other hand, under certain reaction conditions, it cannot be avoided that N-oxides are formed at least intermediary.

The term "stereoisomers" encompasses both optical isomers, such as enantiomers or diastereomers, the latter existing due to more than one centre of chirality in the molecule, as well as geometrical isomers (cis/trans isomers). Depending on the substitution pattern, the compounds of the present invention may have one or more centres of chirality, in which case they may be present as mixtures of enantiomers or diastereomers. The invention provides both the pure enantiomers or diastereomers and their mixtures. Suitable compounds of the invention also include all possible geometrical stereoisomers (cis/trans isomers) and mixtures thereof.

The compounds of the invention may be in the form of solids or liquids or in gaseous form. If the compounds are present as solids, they may be amorphous or may exist in one or more different crystalline states (polymorphs) which may have a different macroscopic properties such as stability or show different biological properties such as activities. The present invention includes both amorphous and crystalline compounds, mixtures of different crystalline states, as well as amorphous or crystalline salts thereof.

The organic moieties mentioned in the above definitions of the variables are—like the term halogen—collective terms for individual listings of the individual group members. The prefix $C_n$-$C_m$ indicates in each case the possible number of carbon atoms in the group.

The term "halogen" denotes in each case fluorine, bromine, chlorine or iodine, in particular fluorine, chlorine or bromine.

The term "alkyl" as used herein and in the alkyl moieties of alkylamino, alkylcarbonyl, alkylthio, alkylsulfinyl, alkylsulfonyl and alkoxyalkyl denotes in each case a straight-chain or branched alkyl group having usually from 1 to 10 carbon atoms, frequently from 1 to 6 carbon atoms, preferably 1 to 4 carbon atoms, more preferably from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl.

The term "haloalkyl" as used herein and in the haloalkyl moieties of haloalkylcarbonyl, haloalkoxycarbonyl, haloalkylthio, haloalkylsulfonyl, haloalkylsulfinyl, haloalkoxy and haloalkoxyalkyl, denotes in each case a straight-chain or branched alkyl group having usually from 1 to 10 carbon atoms, frequently from 1 to 6 carbon atoms, preferably from 1 to 4 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_3$-haloalkyl or $C_1$-$C_2$-haloalkyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "alkoxy" as used herein denotes in each case a straight-chain or branched alkyl group which is bonded via an oxygen atom and has usually from 1 to 10 carbon atoms, frequently from 1 to 6 carbon atoms, preferably 1 to 4 carbon atoms. Examples of an alkoxy group are methoxy, ethoxy, n-propoxy, iso-propoxy, n-butyloxy, 2-butyloxy, iso-butyloxy, tert.-butyloxy, and the like.

The term "alkoxyalkyl" as used herein refers to alkyl usually comprising 1 to 10, frequently 1 to 4, preferably 1 to 2 carbon atoms, wherein 1 carbon atom carries an alkoxy radical usually comprising 1 to 4, preferably 1 or 2 carbon atoms as defined above. Examples are $CH_2OCH_3$, $CH_2$—$OC_2H_5$, 2-(methoxy)ethyl, and 2-(ethoxy)ethyl.

The term "haloalkoxy" as used herein denotes in each case a straight-chain or branched alkoxy group having from 1 to 10 carbon atoms, frequently from 1 to 6 carbon atoms, preferably 1 to 4 carbon atoms, wherein the hydrogen atoms of this group are partially or totally replaced with halogen atoms, in particular fluorine atoms. Preferred haloalkoxy moieties include $C_1$-$C_4$-haloalkoxy, in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluorethoxy, 2,2,2-trichloroethoxy, pentafluoroethoxy and the like.

The term "alkylsulfonyl" (alkyl-S(=O)$_2$—) as used herein refers to a straight-chain or branched saturated alkyl group having 1 to 10 carbon atoms, preferably 1 to 4 carbon atoms (=C$_1$-C$_4$-alkylsulfonyl), preferably 1 to 3 carbon atoms, which is bonded via the sulfur atom of the sulfonyl group at any position in the alkyl group.

The term "haloalkylsulfonyl" as used herein refers to an alkylsulfonyl group as mentioned above wherein the hydrogen atoms are partially or fully substituted by fluorine, chlorine, bromine and/or iodine.

The term "alkylcarbonyl" refers to an alkyl group as defined above, which is bonded via the carbon atom of a carbonyl group (C=O) to the remainder of the molecule.

The term "haloalkylcarbonyl" refers to an alkylcarbonyl group as mentioned above, wherein the hydrogen atoms are partially or fully substituted by fluorine, chlorine, bromine and/or iodine.

The term "alkoxycarbonyl" refers to an alkylcarbonyl group as defined above, which is bonded via an oxygen atom to the remainder of the molecule.

The term "haloalkoxycarbonyl" refers to an alkoxycarbonyl group as mentioned above, wherein the hydrogen atoms are partially or fully substituted by fluorine, chlorine, bromine and/or iodine.

The term "alkenyl" as used herein denotes in each case a singly unsaturated hydrocarbon radical having usually 2 to 10, frequently 2 to 6, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methyl-but-2-en-1-yl, 2-ethylprop-2-en-1-yl and the like.

The term "haloalkenyl" as used herein refers to an alkenyl group as defined above, wherein the hydrogen atoms are partially or totally replaced with halogen atoms.

The term "alkynyl" as used herein denotes in each case a singly unsaturated hydrocarbon radical having usually 2 to 10, frequently 2 to 6, preferably 2 to 4 carbon atoms, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "haloalkynyl" as used herein refers to an alkynyl group as defined above, wherein the hydrogen atoms are partially or totally replaced with halogen atoms.

The term "cycloalkyl" as used herein and in the cycloalkyl moieties of cycloalkoxy and cycloalkylthio denotes in each case a monocyclic cycloaliphatic radical having usually from 3 to 10 or from 3 to 6 carbon atoms, such as cyclopropyl, cyclobutyl, cyclopentyl, cyclohexyl, cycloheptyl, cyclooctyl, cyclononyl and cyclodecyl or cyclopropyl, cyclobutyl, cyclopentyl and cyclohexyl.

The term "halocycloalkyl" as used herein and in the halocycloalkyl moieties of halocycloalkoxy and halocycloalkylthio denotes in each case a monocyclic cycloaliphatic radical having usually from 3 to 10 C atoms or 3 to 6 C atoms, wherein at least one, e.g. 1, 2, 3, 4, or 5 of the hydrogen atoms, are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-,2- and 3-fluorocyclopentyl, 1,2-, 2,2-, 2,3-, 3,3-, 3,4-, 2,5-difluorocyclopentyl, 1-,2- and 3-chlorocyclopentyl, 1,2-, 2,2-, 2,3-, 3,3-, 3,4-, 2,5-dichlorocyclopentyl and the like.

The term "cycloalkoxy" refers to a cycloalkyl group as defined above, which is bonded via an oxygen atom to the remainder of the molecule.

The term "cycloalkylalkyl" refers to a cycloalkyl group as defined above which is bonded via an alkyl group, such as a C$_1$-C$_5$-alkyl group or a C$_1$-C$_4$-alkyl group, in particular a methyl group (=cycloalkylmethyl), to the remainder of the molecule.

The term "cycloalkenyl" as used herein and in the cycloalkenyl moieties of cycloalkenyloxy and cycloalkenylthio denotes in each case a monocyclic singly unsaturated non-aromatic radical having usually from 3 to 10, e.g. 3, or 4 or from 5 to 10 carbon atoms, preferably from 3- to 8 carbon atoms. Exemplary cycloalkenyl groups include cyclopropenyl, cycloheptenyl or cyclooctenyl.

The term "halocycloalkenyl" as used herein and in the halocycloalkenyl moieties of halocycloalkenyloxy and halocycloalkenylthio denotes in each case a monocyclic singly unsaturated non-aromatic radical having usually from 3 to 10, e.g. 3, or 4 or from 5 to 10 carbon atoms, preferably from 3- to 8 carbon atoms, wherein at least one, e.g. 1, 2, 3, 4, or 5 of the hydrogen atoms, are replaced by halogen, in particular by fluorine or chlorine. Examples are 3,3-difluorocyclopropen-1-yl and 3,3-dichlorocyclopropen-1-yl.

The term "cycloalkenylalkyl" refers to a cycloalkenyl group as defined above which is bonded via an alkyl group, such as a C$_1$-C$_5$-alkyl group or a C$_1$-C$_4$-alkyl group, in particular a methyl group (=cycloalkenylmethyl), to the remainder of the molecule.

The term "carbocycle" or "carbocyclyl" includes in general a 3- to 12-membered, preferably a 3- to 8-membered or a 5- to 8-membered, more preferably a 5- or 6-membered mono-cyclic, non-aromatic ring comprising 3 to 12, preferably 3 to 8 or 5 to 8, more preferably 5 or 6 carbon atoms. Preferably, the term "carbocycle" covers cycloalkyl and cycloalkenyl groups as defined above.

The term "heterocycle" or "heterocyclyl" includes in general 3- to 12-membered, preferably 3- to 8-membered or 5- to 8-membered, more preferably 5- or 6-membered, in particular 6-membered monocyclic heterocyclic non-aromatic radicals. The heterocyclic non-aromatic radicals usually comprise 1, 2, 3, 4, or 5, preferably 1, 2 or 3 heteroatoms selected from N, O and S as ring members, where S-atoms as ring members may be present as S, SO or SO$_2$. Examples of 5- or 6-membered heterocyclic radicals comprise saturated or unsaturated, non-aromatic heterocyclic rings, such as oxiranyl, oxetanyl, thietanyl, thietanyl-S-oxid (S-oxothietanyl), thietanyl-S-dioxid (S-dioxothiethanyl), pyrrolidinyl, pyrrolinyl, pyrazolinyl, tetrahydrofuranyl, dihydrofuranyl, 1,3-dioxolanyl, thiolanyl, S-oxothiolanyl, S-dioxothiolanyl, dihydrothienyl, S-oxodihydrothienyl, S-dioxodihydrothienyl, oxazolidinyl, oxazolinyl, thiazolinyl, oxathiolanyl, piperidinyl, piperazinyl, pyranyl, dihydropyranyl, tetrahydropyranyl, 1,3- and 1,4-dioxanyl, thiopyranyl, S.oxothiopyranyl, S-dioxothiopyranyl, dihydrothiopyranyl, S-oxodihydrothiopyranyl, S-dioxodihydrothiopyranyl, tetrahydrothiopyranyl, S-oxotetrahydrothiopyranyl, S-dioxotetrahydrothiopyranyl, morpholinyl, thiomorpholinyl, S-oxothiomorpholinyl, S-dioxothiomorpholinyl, thiazinyl and the like. Examples for heterocyclic ring also comprising 1 or 2 carbonyl groups as ring members comprise pyrrolidin-2-onyl, pyrrolidin-2,5-dionyl, imidazolidin-2-onyl, oxazolidin-2-onyl, thiazolidin-2-onyl and the like.

The term "hetaryl" includes monocyclic 5- or 6-membered heteroaromatic radicals comprising as ring members 1, 2, 3, or 4 heteroatoms selected from N, O and S. Examples of 5- or 6-membered heteroaromatic radicals include pyridyl, i.e. 2-, 3-, or 4-pyridyl, pyrimidinyl, i.e. 2-, 4-, or 5-pyrimidinyl, pyrazinyl, pyridazinyl, i.e. 3- or 4-pyridazinyl, thienyl, i.e. 2- or 3-thienyl, furyl, i.e. 2- or 3-furyl, pyrrolyl, i.e. 2- or 3-pyrrolyl, oxazolyl, i.e. 2-, 3-, or 5-oxazolyl, isoxazolyl, i.e. 3-, 4-, or 5-isoxazolyl, thiazolyl, i.e. 2-, 3- or 5-thiazolyl, isothiazolyl, i.e. 3-, 4-, or 5-isothiazolyl, pyrazolyl, i.e. 1-, 3-, 4-, or 5-pyrazolyl, i.e. 1-, 2-, 4-, or 5-imidazolyl, oxadiazolyl, e.g. 2- or 5-[1,3,4]oxadiazolyl, 4- or 5-(1,2,3-oxadiazol)yl, 3- or 5-(1,2,4-oxadiazol)yl, 2- or 5-(1,3,4-thiadiazol)yl, thiadiazolyl, e.g. 2- or 5-(1,3,4-thiadiazol)yl, 4- or 5-(1,2,3-thiadiazol)yl, 3- or 5-(1,2,4-thiadiazol)yl, triazolyl, e.g. 1H-, 2H- or 3H-1,2,3-triazol-4-yl, 2H-triazol-3-yl, 1H-, 2H-, or 4H-1,2,4-triazolyl and tetrazolyl, i.e. 1H- or 2H-tetrazolyl. The term "hetaryl" also includes bicyclic 8 to 10-membered heteroaromatic radicals comprising as ring members 1, 2 or 3 heteroatoms selected from N, O and S, wherein a 5- or 6-membered heteroaromatic ring is fused to a phenyl ring or to a 5- or 6-membered heteroaromatic radical. Examples of a 5- or 6-membered heteroaromatic ring fused to a phenyl ring or to a 5- or 6-membered heteroaromatic radical include benzofuranyl, benzothienyl, indolyl, indazolyl, benzimidazolyl, benzoxathiazolyl, benzoxadiazolyl, benzothiadiazolyl, benzoxazinyl, chinolinyl, isochinolinyl, purinyl, 1,8-naphthyridyl, pteridyl, pyrido[3,2-d]pyrimidyl or pyridoimidazolyl and the like. These fused hetaryl radicals may be bonded to the remainder of the molecule via any ring atom of 5- or 6-membered heteroaromatic ring or via a carbon atom of the fused phenyl moiety.

The term "aryl" includes mono-, bi- or tricyclic aromatic radicals having usually from 6 to 14, preferably 6, 10, or 14 carbon atoms. Exemplary aryl groups include phenyl, naphthyl and anthracenyl. Phenyl is preferred as aryl group.

The terms "heterocyclyloxy", "hetaryloxy", and "phenoxy" refer to heterocyclyl, hetaryl, and phenyl, which are bonded via an oxygen atom to the remainder of the molecule.

The terms "heterocyclylsulfonyl", "hetarylsulfonyl", and "phenylsulfonyl" refer to heterocyclyl, hetaryl, and phenyl, respectively, which are bonded via the sulfur atom of a sulfonyl group to the remainder of the molecule.

The terms "heterocyclylcarbonyl", "hetarylcarbonyl", and "phenylcarbonyl" refer to heterocyclyl, hetaryl, and phenyl, respectively, which are bonded via the carbon atom of a carbonyl group (C=O) to the remainder of the molecule.

The terms "heterocyclylalkyl" and "hetarylalkyl" refer to heterocyclyl or hetaryl, respectively, as defined above which are bonded via a $C_1$-$C_5$-alkyl group or a $C_1$-$C_4$-alkyl group, in particular a methyl group (=heterocyclylmethyl or hetarylmethyl, respectively), to the remainder of the molecule.

The term "phenylalkyl" refers to phenyl which is bonded via a $C_1$-$C_5$-alkyl group or a $C_1$-$C_4$-alkyl group, in particular a methyl group (=arylmethyl or phenylmethyl), to the remainder of the molecule, examples including benzyl, 1-phenylethyl, 2-phenylethyl, etc.

The terms "alkylene" refers to alkyl as defined above, which represents a linker between molecule and a substituent.

Preferred embodiments regarding the processes A, B, C, and D of the invention are described hereinafter.

In general, the reaction steps performed in the processes A, B, C, and D as described in detail hereinafter are performed in reaction vessels customary for such reactions, the reactions being carried out in a continuous, semi-continuous or batchwise manner.

In general, the particular reactions will be carried out under atmospheric pressure. The reactions may, however, also be carried out under reduced pressure.

The temperatures and the duration times of the reactions may be varied in broad ranges, which the person skilled in the art knows from analogous reactions. The temperatures often depend on the reflux temperature of the solvents. Other reactions are preferably performed at room temperature, i.e. at about 25° C., or under ice cooling, i.e. at about 0° C. The end of the reaction can be monitored by methods known to a person skilled in the art, e.g. thin layer chromatography or HPLC.

If not otherwise indicated, the molar ratios of the reactants, which are used in the reactions, are in the range of from 0.2:1 to 1:0.2, preferably from 0.5:1 to 1:0.5, more preferably from 0.8:1 to 1:0.8. Preferably, equimolar amounts are used.

If not otherwise indicated, the reactants can in principle be contacted with one another in any desired sequence.

The person skilled in the art knows when the reactants or reagents are moisture sensitive, so that the reaction should be carried out under protective gases such as under a nitrogen atmosphere, and dried solvents should be used.

The person skilled in the art also knows the best work-up of the reaction mixture after the end of the reaction.

In the following, preferred embodiments regarding process A of the invention are provided. It is to be understood that the preferred embodiments mentioned above and those still to be illustrated below of process A of the invention are to be understood as preferred alone or in combination with each other.

As already indicated above, the present invention relates in a first aspect to the process A of preparing a pyridazine amine compound of formula V or a salt, tautomer, or N-oxide thereof

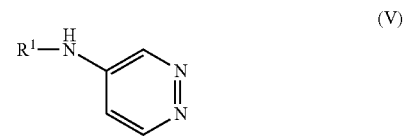

comprising the step of reacting (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b)

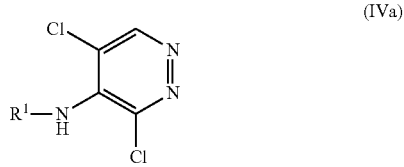

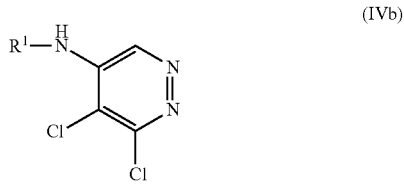

with hydrogen in the presence of a hydrogenation catalyst, wherein $R^1$ is H, $C_1$-$C_2$-alkyl, or $C_1$-$C_2$-alkoxy-$C_1$-$C_2$-alkyl.

The reaction step underlying process A corresponds to step (iv) in the above reaction sequence.

The reaction step (iv) can only be performed in the presence of a hydrogenation catalyst.

As used herein, the term "hydrogenation catalyst" covers heterogeneous and homogeneous hydrogenation catalysts, but preferably refers to heterogeneous catalysts. It is known in the art that platinum, palladium, rhodium, and ruthenium form highly active catalysts. Non-precious metal catalysts, such as catalysts based on nickel (such as Raney nickel and Urushibara nickel) are economical alternatives. Preferred hydrogenation catalysts according to the invention are provided further below.

As a side product of reaction step (iv), hydrogen chloride is produced.

Nevertheless, in a preferred embodiment of process A, the reaction is performed in the absence of a HCl scavenger. It has surprisingly been found that the compounds of formula V are obtained in higher yields, if a HCl scavenger is not present in the reaction mixture.

As used herein, the term "HCl scavenger" refers to a chemical substance, which is added to a reaction mixture in order to remove or de-activate hydrogen chloride (HCl). Preferred HCl scavengers include bases, buffers, and precursors of ionic liquids, which are defined in further detail below. Of particular interest is the capability of HCl scavengers to bind protons. Preferred HCl scavengers are provided below.

Preferably, it is to be understood that the term "HCl scavenger" as used herein refers to a chemical substance, which is added to the reaction mixture, and does not include the starting materials of the reaction, i.e. the compounds of formula (IVa) or (IVb).

It is therefore preferred that the reaction step (iv) is carried out in the absence of any additionally provided chemical substance, which functions as a HCl scavenger.

As the reaction step (iv) is preferably carried out in the absence of a HCl scavenger, the produced HCl is still in the reaction mixture, when the hydrogenation catalyst is removed.

Therefore, in another preferred embodiment of process A, a HCl scavenger is added after removal of the hydrogenation catalyst. Preferably, the HCl scavenger is provided without water. It has been found that it is advantageous to keep the reaction product, i.e. the compounds of formula V, water-free to avoid a loss of the compounds in the aqueous phase, allow for an easier work-up, and to avoid the necessity of drying the compounds prior to further reactions.

The HCl scavenger, which is preferably only added after removal of the hydrogenation catalyst, may principally be selected from bases, buffers, precursors of ionic liquids, and combinations thereof.

Bases include alkali metal and alkaline earth metal hydroxides, alkali metal and alkaline earth metal oxides, alkali metal and alkaline earth metal hydrides, alkali metal amides, alkali metal and alkaline earth metal carbonates, alkali metal bicarbonates, alkali metal alkyls, alkylmagnesium halides, alkali metal and alkaline earth metal alcoholates, and nitrogen containing bases including tertiary amines, pyridines, bicyclic amines, ammonia, and primary amines.

Buffers include aqueous and non-aqueous buffers, and are preferably non-aqueous buffers. Preferred buffers include buffers based on acetate or formate, e.g. sodium acetate or ammonium formate.

Precursors of ionic liquids include imidazoles.

In a preferred embodiment of process A of the present invention, the HCl scavenger is selected from the group consisting of bases including alkali metal and alkaline earth metal hydroxides, alkali metal and alkaline earth metal oxides, alkali metal and alkaline earth metal hydrides, alkali metal amides, alkali metal and alkaline earth metal carbonates, alkali metal bicarbonates, alkali metal alkyls, alkylmagnesium halides, alkali metal and alkaline earth metal alcoholates, nitrogen containing bases including tertiary amines, pyridines, bicyclic amines, ammonia, and primary amines, and combinations thereof; buffers including sodium acetate and/or ammonium formate; precursors of ionic liquids including imidazoles; and combinations thereof.

In one preferred embodiment, the HCl scavenger comprises at least one base.

In one particularly preferred embodiment, the base is selected from alkali metal and alkaline earth metal hydroxides, in particular from the group consisting of lithium hydroxide, sodium hydroxide, potassium hydroxide, and calcium hydroxide.

In another particularly preferred embodiment, the base is selected from alkali metal and alkaline earth metal oxides, in particular from the group consisting of lithium oxide, sodium oxide, calcium oxide, and magnesium oxide.

In another particularly preferred embodiment, the base is selected from alkali metal and alkaline earth metal hydrides, in particular from the group consisting of lithium hydride, sodium hydride, potassium hydride, and calcium hydride.

In another particularly preferred embodiment, the base is selected from alkali metal amides, in particular from the group consisting of lithium amide, sodium amide, and potassium amide. In another particularly preferred embodiment, the base is selected from alkali metal and alkaline earth metal carbonates, in particular from the group consisting lithium carbonate and calcium carbonate.

In another particularly preferred embodiment, the base is selected from alkali metal bicarbonates, and is preferably sodium bicarbonate.

In another particularly preferred embodiment, the base is selected from alkali metal alkyls, in particular from the group consisting of methyllithium, butyllithium, and phenyllithium.

In another particularly preferred embodiment, the base is selected from alkylmagnesium halides, and is preferably methylmagnesiumchloride In another particularly preferred embodiment, the base is selected from alkali metal and alkaline earth metal alcoholates, in particular from the group consisting of sodium methanolate, sodium ethanolate, potassium ethanolate, potassium tert-butanolate, and dimethoxymagnesium.

In another particularly preferred embodiment, the base is a tertiary amine, in particular trimethylamine, triethylamine, diisopropylethylamine, or N-methylpiperidine.

In another particularly preferred embodiment, the base is a pyridine including substituted pyridines such as collidine, lutidine and 4-dimethylaminopyridine.

In another particularly preferred embodiment, the base is a bicyclic amine.

In another particularly preferred embodiment, the base is ammonia.

In another particularly preferred embodiment, the base is a primary amine, in particular ethylamine.

In a most preferred embodiment of the process A of the invention, the HCl scavenger is potassium hydroxide or any one of the above defined carbonates.

The bases may be used in equimolar quantities, in excess or, where appropriate, as solvents.

In another preferred embodiment, the HCl scavenger comprises at least one buffer.

In a particularly preferred embodiment, the buffer is anhydrous sodium acetate or anhydrous ammonium formate.

In another preferred embodiment, the HCl scavenger comprises a precursor of an ionic liquid.

In a particularly preferred embodiment, the precursor of the ionic liquid is an imidazole compound, which forms an ionic liquid after having reacted with the HCl, which is set free in the hydrogenation/dehalogenation reaction. A non-polar organic phase comprising the desired pyridazine amine compound can then be easily separated from the newly formed ionic liquid.

As already indicated above, any hydrogenation catalysts known in the art may be used for reaction step (iv), in particular heterogeneous hydrogenation catalysts.

Preferred hydrogenation catalysts include platinum, palladium, rhodium, ruthenium, nickel, or cobalt on carriers such as carbon.

In a preferred embodiment of process A of the present invention, the hydrogenation catalyst is selected from the group consisting of platinum or palladium on a carrier, Raney nickel, and Raney cobalt, and is preferably platinum or palladium on carbon.

Optionally, the catalyst may be doped with sulfur or selenium. This can enhance the selectivity of the catalyst.

In a particularly preferred embodiment, the hydrogenation catalyst is palladium or platinum on carbon, wherein the palladium or platinum content is preferably in the range of from 0.1 to 15% by weight, more preferably from 0.5 to 10% by weight based on the carrier material.

In another particularly preferred embodiment, the amount of palladium or platinum used is from 0.001 to 1% by weight, preferably from 0.01 to 0.1% by weight based on the starting material.

In one particularly preferred embodiment, the hydrogenation catalyst is palladium on carbon, wherein the palladium content is preferably in the range of from 0.1 to 15% by weight, more preferably from 0.5 to 10% by weight based on the carrier material. Furthermore, it is particularly preferred that the amount of palladium used in the reaction step (iv) is from 0.001 to 1% by weight, preferably from 0.01 to 0.1% by weight based on the starting material. It is especially preferred that 10% Pd/C is used in amount of 0.01 to 0.1% by weight based on the amount of the starting material.

In another particularly preferred embodiment, the hydrogenation catalyst is platinum on carbon, wherein the platinum content is preferably of from 0.1 to 15% by weight, more preferably from 0.5 to 10% by weight based on the carrier material. Furthermore, it is particularly preferred that the amount of platinum used in the reaction step (iv) is from 0.001 to 1, preferably from 0.01 to 0.1% by weight based on the starting material. It is especially preferred that 10% Pt/C is used in amount of 0.01 to 0.1% by weight based on the amount of the starting material.

In the batchwise hydrogenation, the catalyst is preferably used in the form of a powder. In a continuous hydrogenation, the catalyst used on the carrier material carbon is platinum or palladium.

After a reaction cycle, the catalyst can be filtered off and reused without noticeable loss of activity.

With regard to the starting materials of reaction step (iv), it is emphasized that either (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b) may be used.

In a preferred embodiment of process A, a mixture of (a) and (b) is used.

The substituent $R^1$ in the compounds of formulae IVa, IVb, and V is preferably selected from the group consisting of $CH_3$, $CH_2CH_3$, and $CH_2OCH_3$.

In a preferred embodiment of process A, $R^1$ in the compounds of formulae IVa, IVb, and V is $CH_2CH_3$.

In a particularly preferred embodiment of process A, a mixture of (a) and (b) is used, and $R^1$ in the compounds of formulae IVa, IVb, and V is selected from the group consisting of $CH_3$, $CH_2CH_3$, and $CH_2OCH_3$, and is preferably $CH_2CH_3$.

Mild reaction conditions are preferred for reaction step (iv).

In a preferred embodiment, the applied hydrogen pressure is in the range of from 0.1 to 10 bar, preferably in the range of from 0.1 to 1 bar, more preferably in the range of from 0.1 to 0.5 bar. Higher pressures in the range of from 0.6 bar to 10 bar, preferably 1 bar to 5 bar can be advantageous if the starting material contains impurities in an amount of more than 2% by weight or more than 5% by weight.

In a preferred embodiment, the reaction temperature is kept within a range of from 20 to 100° C., preferably in the range of from 20 to 65° C. It is preferred that the reaction mixture is heated to 30 to 40° C. after the pressure reactor, wherein the reaction is preferably performed, is filled with hydrogen. However, as the hydrogenation reaction is exothermic, it can be required to cool the reaction mixture afterwards to keep the temperature preferably below 60° C. A reaction temperature in the range of from 50 to 60° C. is particularly preferred.

The reaction times may vary over a broad range. Preferred reaction times are in the range of from 1 hour to 12 hours, preferably in the range of from 3 hours to 6 hours, e.g. 4 or 5 hours.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform and chlorobenzene; alcohols such as methanol, ethanol, n-propanol, isopropanol, n-butanol and tert-butanol; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

Preferred solvents are protic solvents, preferably alcohols selected from the group consisting of such as methanol, ethanol, n-propanol, isopropanol, n-butanol and tert-butanol.

In a preferred embodiment, the solvent is a $C_1$-$C_4$-alcohol, in particular ethanol.

As has been set out above, process A may not only comprise reaction step (iv), but also other reaction steps of the above described reaction sequence.

In particular, process A may optionally further comprise step (iii) and optionally also step (ii), wherein steps (ii) and (iiii) may be carried out separately or together as steps (ii)+(iii) in a one-pot reaction. In addition, process A may optionally further comprise step (i). Furthermore, it is to be understood that process A may optionally further comprise step (v).

In one embodiment of process A, the process further comprises reaction steps (ii)+(iii), i.e. the step of preparing (a) the dichloropyridazine amine compound of formula IVa or a salt, tautomer, or N-oxide thereof, or (b) the dichloropyridazine amine compound of formula IVb or a salt, tautomer, or N-oxide thereof, or (c) the mixture of (a) and (b)

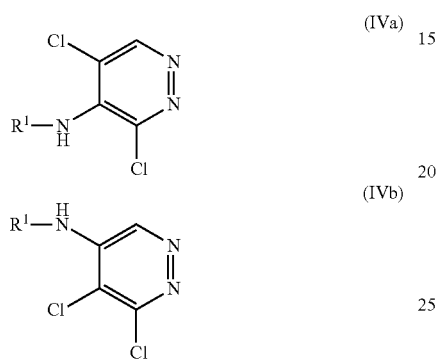

(IVa)

(IVb)

in a one-pot reaction comprising the steps of
reacting a compound of formula II

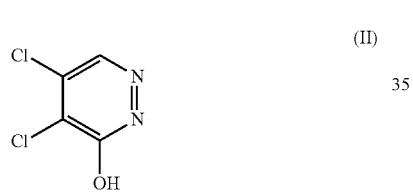

(II)

with POCl$_3$, and
reacting the resulting crude reaction product with an amine compound R$^1$—NH$_2$ or a salt thereof, wherein R$^1$ is H, C$_1$-C$_2$-alkyl, or C$_1$-C$_2$-alkoxy-C$_1$-C$_2$-alkyl.

As indicated above, the one-pot reaction is advantageous, as the intermediary obtained trichloropyridazine compound of formula III, which is irritating, does not have to be isolated.

It is to be understood that (a) or (b) or a mixture of (a) and (b) may be obtained in steps (ii)+(iii).

In a preferred embodiment, a mixture of (a) and (b) is obtained.

The substituent R$^1$ in the compounds of formulae IVa and IVb, and the amine compound R$^1$—NH$_2$ is preferably selected from the group consisting of CH$_3$, CH$_2$CH$_3$, and CH$_2$OCH$_3$.

In a preferred embodiment, R$^1$ in the compounds of formulae IVa and IVb, and the amine compound R$^1$—NH$_2$ is CH$_2$CH$_3$.

In a particularly preferred embodiment, a mixture of (a) and (b) is obtained, and R$^1$ in the compounds of formulae IVa and IVb, and the amine compound R$^1$—NH$_2$ is selected from the group consisting of CH$_3$, CH$_2$CH$_3$, and CH$_2$OCH$_3$, and is preferably CH$_2$CH$_3$.

It is to be understood that the compound of formula II may also be present in the form of its pyridazone tautomer.

The reaction conditions for steps (ii) and (iii), which are performed subsequently in the one-pot reaction as defined above, without isolating the intermediary obtained compound of formula III, are defined in further detail below.

In an alternative embodiment of process A, the process further comprises reaction step (iii), i.e. the step of preparing (a) the dichloropyridazine amine compound of formula IVa or a salt, tautomer, or N-oxide thereof, or (b) the dichloropyridazine amine compound of formula IVb or a salt, tautomer, or N-oxide thereof, or (c) the mixture of (a) and (b)

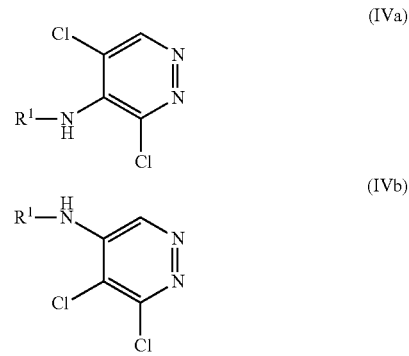

(IVa)

(IVb)

by reacting a trichloropyridazine compound of formula III

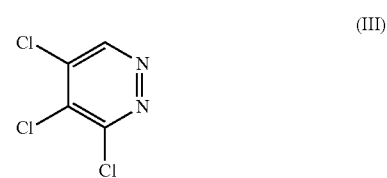

(III)

with an amine compound R$^1$—NH$_2$ or a salt thereof,
wherein R$^1$ is H, C$_1$-C$_2$-alkyl, or C$_1$-C$_2$-alkoxy-C$_1$-C$_2$-alkyl, and wherein the process optionally further comprises reaction step (ii), i.e. the step of preparing the trichloropyridazine compound of formula III

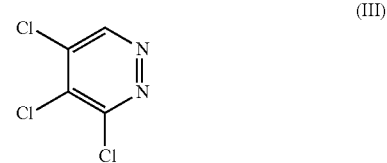

(III)

by reacting a compound of formula II

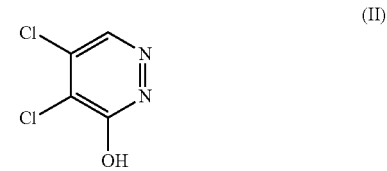

(II)

with POCl$_3$.

According to this embodiment, the compound of formula III is isolated, which may e.g. be done by precipitation.

It is to be understood that (a) or (b) or a mixture of (a) and (b) may be obtained in steps (iii).

In a preferred embodiment, a mixture of (a) and (b) is obtained.

The substituent $R^1$ in the compounds of formulae IVa and IVb, and the amine compound $R^1$—$NH_2$ is preferably selected from the group consisting of $CH_3$, $CH_2CH_3$, and $CH_2OCH_3$.

In a preferred embodiment, $R^1$ in the compounds of formulae IVa and IVb, and the amine compound $R^1$—$NH_2$ is $CH_2CH_3$.

In a particularly preferred embodiment, a mixture of (a) and (b) is obtained, and $R^1$ in the compounds of formulae IVa and IVb, and the amine compound $R^1$—$NH_2$ is selected from the group consisting of $CH_3$, $CH_2CH_3$, and $CH_2OCH_3$, and is preferably $CH_2CH_3$.

As already indicated above, it is to be understood that the compound of formula II may also be present in the form of its pyridazone tautomer.

The reaction conditions for steps (ii) and (iii), which also apply to the situation, wherein the steps are performed as steps (ii)+(iii) in a one-pot reaction are defined hereinafter.

The reaction conditions for step (ii) are preferably as follows.

In a preferred embodiment of reaction step (ii), $POCl_3$ is used in an excess.

In another preferred embodiment, $POCl_3$ is used in an amount of at least 1.5 mol per mol of the compound of formula II.

In one particularly preferred embodiment, $POCl_3$ is used in an amount of from 1.5 to 2.0 mol per mol of the compound of formula II.

In another particularly preferred embodiment, $POCl_3$ is used in an amount of more than 2.0 to 10 mol per mol of the compound of formula II, preferably in an amount of from 4.0 to 6.0 mol, in particular in an amount of from 4.8 to 5.2 mol per mol of the compound of formula II.

In yet another particularly preferred embodiment, $POCl_3$ is used as a solvent for reaction step (ii).

It is preferred that the reaction step (ii) is performed in the absence of a solvent.

It is further preferred that the reaction is performed in a protective gas atmosphere, e.g. under nitrogen.

The reaction temperature may be in the range of from 60° C. to 130° C., preferably in the range of from 100° C. to 125° C.

The reaction times may vary over a broad range, and are preferably in a range of from 1 hour to 24 hours, preferably in the range of from 1 hour to 5 hours, more preferably in the range of from 1 hour to 2 hours.

After the reaction, the excess $POCl_3$ may be removed under reduced pressure. Afterwards, water is preferably added to the reaction mixture upon cooling so that the temperature preferably does not exceed 30° C.

The trichloropyridazine compound of formula III can be isolated as a precipitate from the aqueous phase, or by transferring the compound of formula III into an organic phase, and removing the organic solvent.

Preferred organic solvents in this connection include dichloromethane, iso-butanol, ethyl acetate, and butyl acetate, in particular butyl acetate.

With regard to the preparation and isolation of the trichloropyridazine compound of formula III, reference is e.g. made to WO 2013/004984, WO 2014/091368, WO 99/64402, WO 2002/100352, and Russian Journal of Applied Chemistry, Vol. 77, No. 12, 2004, pp. 1997-2000.

If the one-pot reaction procedure as defined above is performed, the step of isolating the trichloropyridazine compound of formula III can be omitted. Instead, the trichloropyridazine is transferred to an organic phase and directly used in the next reaction step.

Preferred organic solvents in this connection include dichloromethane, iso-butanol, ethyl acetate, and butyl acetate, in particular butyl acetate.

The organic phase may optionally be washed with a sodium hydroxide solution in water (e.g. a 10% NAOH aqueous solution) and/or water prior to further use.

The reaction conditions for step (iii) are preferably as follows.

Depending on the substituent $R^1$, the amine compound $R^1$—$NH_2$ may be in gaseous or liquid or solid form. If the amine compound $R^1$—$NH_2$ is in gaseous form, it may either be provided as a solution or as a gas.

A particularly preferred amine compound is ethylamine as already indicated above.

Suitable solvents include protic solvents, preferably water or $C_1$-$C_4$-alcohols such as methanol, ethanol, n-propanol, isopropanol, n-butanol and tert-butanol, especially ethanol.

In one preferred embodiment, the solvent, wherein the amine compound $R^1$—$NH_2$ is provided, is water. Suitable concentrations are in the range of from 10 to 100 wt.-% based on the total weight of the solution, preferably in the range of from 40 to 90 wt.-%, more preferably 60 to 80%, most preferably 66 to 72 wt.-%.

In a particularly preferred embodiment, the amine compound $R^1$—$NH_2$ is ethylamine and is provided as a solution in water with a concentration in the range of from 60 to 80% based on the total weight of the solution, preferably 66 to 72 wt.-%.

It is a surprising finding of the present invention that the presence of water in the reaction mixture does not negatively affect the yields of reaction step (iii).

In another preferred embodiment, the amine compound $R^1$—$NH_2$ is provided in gaseous form and is introduced into the reaction mixture by bubbling it into the solvent, wherein the reaction step (iii) shall be performed, and wherein trichloropyridazine compound of formula III may already be dissolved. In this connection, preferred solvents include protic solvents, preferably alcohols selected from the group consisting of methanol, ethanol, n-propanol, isopropanol, n-butanol and tert-butanol. Especially preferred is ethanol as the solvent. Furthermore, preferred solvents, wherein the gaseous amine compound $R^1$—$NH_2$ may be dissolved for reaction step (iii), generally include toluene, THF, and ethanol.

It is preferred that an excess of the amine compound $R^1$—$NH_2$ is used.

In a preferred embodiment, the amine compound $R^1$—$NH_2$ is used in an amount of from 1.5 to 10 mol per mol of the compound of formula III, preferably in an amount of from 2.0 to 6.0 mol, in particular in an amount of from 2.0 to 3.0 mol per mol of the compound of formula III.

Suitable solvents for the reaction include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform and chlorobenzene; alcohols such as methanol, ethanol, n-propanol, isopropanol, n-butanol and tert-butanol; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

It is particularly preferred that the reaction is performed in a mixture of the solvents, in which the starting materials are provided, e.g. a mixture of water and butylacetate.

Alternatively, it is particularly preferred that the reaction is performed in protic solvents preferably alcohols selected from the group consisting of methanol, ethanol, n-propanol, isopropanol, n-butanol and tert-butanol, especially ethanol, in particular if the amine compound is provided in gaseous form. The reaction step (iii) will then be performed in this protic solvent, and, optionally, also reaction step step (iv) may be directly performed afterwards in a one-pot reaction, optionally with the excess of the amine compound being used as the HCl scavenger.

The reaction may be carried out at temperatures in the range of from 0° C. to 140° C., preferably in a range of from 25° C. to 60° C., more preferably in a range of from 30° C. to 50° C.

In connection with the amine compound $R^1$—$NH_2$ as defined herein, especially with the amine compound $R^1$—$NH_2$ being ethylamine, the following reaction temperatures are particularly preferred.

In one embodiment, reaction step (iii) is performed at a temperature of 100° C. or less.

In another embodiment, reaction step (iii) is performed at a temperature of 80° C. or less.

In another embodiment, reaction step (iii) is performed at a temperature of 70° C. or less.

In another embodiment, reaction step (iii) is performed at a temperature of 60° C. or less.

In one embodiment, reaction step (iii) is performed at a temperature of from 0° C. to 100° C.

In another embodiment, reaction step (iii) is performed at a temperature of from 0° C. to 80° C.

In another embodiment, reaction step (iii) is performed at a temperature of from 0° C. to 70° C.

In another embodiment, reaction step (iii) is performed at a temperature of from 0° C. to 60° C.

In a preferred embodiment, reaction step (iii) is performed at a temperature of from 20° C. to 80° C.

In another preferred embodiment, reaction step (iii) is performed at a temperature of from 20° C. to 70° C.

In another preferred embodiment, reaction step (iii) is performed at a temperature of from 20° C. to 60° C.

In a particularly preferred embodiment, reaction step (iii) is performed at a temperature of from 25° C. to 60° C.

The reaction times vary over a broad range, e.g. in a range of from 1 hour to 4 days. Preferably, the reaction time is in the range of from 1 hour to 24 hours, in particular from 1 hour to 12 hours. More preferably, the reaction time is in the range of from 1 hour to 5 hours, preferably from 3 hours to 4 hours.

In connection with reaction step (iii), reference is also made to U.S. Pat. No. 4,728,355.

As already indicated above, process A may optionally further comprise step (i) to provide the compound of formula II.

In one embodiment of process A, the process comprises in addition to steps (ii) and (iii), either performed separately or as a one-pot reaction, also step (i), i.e. the process further comprises the step of preparing the compound of formula II

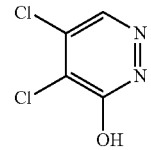

(II)

by reacting mucochloric acid I

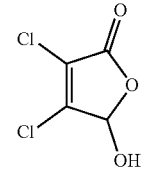

(I)

with hydrazine or a salt thereof.

The reaction conditions for step (iii) are preferably as follows.

The reactants are preferably provided in similar amounts, e.g. in a molar ratio of from 1.5:1 to 1:1.5, preferably in equimolar amounts.

Hydrazine is preferably provided in the form of a salt, preferably as hydrazine sulfate.

Suitable solvents include protic solvents such as water.

The reaction mixture is preferably heated to 100° C., until a precipitate forms.

For further details, reference is made to U.S. Pat. No. 4,728,355.

As already indicated above, process A may optionally further comprise step (v).

In one embodiment of process A, the process further comprises step (v), i.e. the process further comprises the step of converting the pyridazine amine compound of formula V or a salt, tautomer, or N-oxide thereof into a compound of formula VII or a stereoisomer, salt, tautomer, or N-oxide thereof

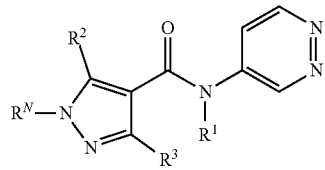

(VII)

by reacting the pyridazine amine compound of formula V or a salt, tautomer, or N-oxide thereof

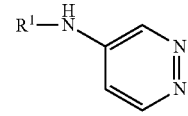

(V)

with a compound of formula VI or a stereoisomer, salt, tautomer, or N-oxide thereof

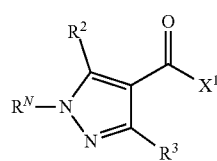

wherein $R^1$ is H, $C_1$-$C_2$-alkyl, or $C_1$-$C_2$-alkoxy-$C_1$-$C_2$-alkyl, and wherein $R^2$ is H, halogen, CN, $NO_2$, $C_1$-$C_{10}$-alkyl, $C_2$-$C_{10}$-alkenyl, or $C_2$-$C_{10}$-alkynyl, wherein the 3 last mentioned radicals may be unsubstituted, may be partially or fully halogenated or may carry 1, 2 or 3 identical or different substituents $R^x$, or $OR^a$, $SR^a$, $C(Y)R^b$, $C(Y)OR^c$, $S(O)R^d$, $S(O)_2R^d$, $NR^eR^f$, $C(Y)NR^gR^h$, heterocyclyl, hetaryl, $C_3$-$C_{10}$-cycloalkyl, $C_3$-$C_{10}$-cycloalkenyl or phenyl, wherein the five last mentioned radicals may be unsubstituted or may carry 1, 2, 3, 4 or 5 identical or different substituents selected from the radicals $R^y$ and $R^x$;

$R^3$ is H, halogen, CN, $NO_2$, $C_1$-$C_{10}$-alkyl, $C_2$-$C_{10}$-alkenyl, or $C_2$-$C_{10}$-alkynyl, wherein the 3 last mentioned radicals may be unsubstituted, may be partially or fully halogenated or may carry 1, 2 or 3 identical or different substituents $R^x$, or $OR^a$, $SR^a$, $C(Y)R^b$, $C(Y)OR^c$, $S(O)R^d$, $S(O)_2R^d$, $NR^eR^f$, $C(Y)NR^gR^h$, heterocyclyl, hetaryl, $C_3$-$C_{10}$-cycloalkyl, $C_3$-$C_{10}$-cycloalkenyl or phenyl, wherein the five last mentioned radicals may be unsubstituted or may carry 1, 2, 3, 4 or 5 identical or different substituents selected from the radicals $R^y$ and $R^x$;

$R^N$ is H, CN, $NO_2$, $C_1$-$C_{10}$-alkyl, $C_2$-$C_{10}$-alkenyl, or $C_2$-$C_{10}$-alkynyl, wherein the three last mentioned radicals may be unsubstituted, may be partially or fully halogenated or may carry 1, 2 or 3 identical or different substituents $R^x$, or $OR^a$, $SR^a$, $C(Y)R^b$, $C(Y)OR^c$, $S(O)R^d$, $S(O)_2R^d$, $NR^eR^f$, $C(Y)NR^gR^h$, $S(O)_mNR^eR^f$, $C(Y)NR^iNR^eR^f$, $C_1$-$C_5$-alkylen-$OR^a$, $C_1$-$C_5$-alkylen-CN, $C_1$-$C_5$-alkylen-C(Y)$R^b$, $C_1$-$C_5$-alkylen-C(Y)$OR^c$, $C_1$-$C_5$-alkylen-$NR^eR^f$, $C_1$-$C_5$-alkylen-C(Y)$NR^gR^h$, $C_1$-$C_5$-alkylen-$S(O)^mR^d$, $C_1$-$C_5$-alkylen-$S(O)_mNR^eR^f$, $C_1$-$C_5$-alkylen-$NR^iNR^eR^f$, heterocyclyl, hetaryl, $C_3$-$C_{10}$-cycloalkyl, $C_3$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_3$-$C_{10}$-cycloalkenyl-$C_1$-$C_5$-alkyl, phenyl-$C_1$-$C_5$-alkyl, or phenyl, wherein the rings of the ten last mentioned radicals may be unsubstituted or may carry 1, 2, 3, 4 or 5 identical or different substituents $R^y$;

and wherein $R^a$, $R^b$, $R^c$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl, and hetaryl-$C_1$-$C_4$-alkyl, wherein the ring in the six last mentioned radicals may be unsubstituted or may carry 1, 2, 3, 4, or 5 substituents which, independently of each other, are selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl, and hetaryl-$C_1$-$C_4$-alkyl, wherein the ring in the six last mentioned radicals may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^e$, $R^f$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkylsulfonyl, $C_1$-$C_4$-haloalkylsulfonyl, heterocyclyl, heterocyclyl-$C_1$-$C_4$-alkyl, heterocyclylcarbonyl, heterocyclylsulfonyl, phenyl, phenylcarbonyl, phenylsulfonyl, hetaryl, hetarylcarbonyl, hetarylsulfonyl, phenyl-$C_1$-$C_4$-alkyl, and hetaryl-$C_1$-$C_4$-alkyl, wherein the ring in the twelve last mentioned radicals may be unsubstituted or may carry 1, 2, 3, 4, or 5 substituents which, independently of each other, are selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^g$, $R^h$ are independently of each other selected from H, $C_1$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl, and hetaryl-$C_1$-$C_4$-alkyl, wherein the ring in the six last mentioned radicals may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^i$ is selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, and phenyl-$C_1$-$C_4$-alkyl, wherein the phenyl ring in the two last mentioned radicals may be unsubstituted or may carry 1, 2, 3, 4, or 5 substituents which are independently of each other selected from halogen, CN, $NO_2$, $C_1$-$C_4$-alkyl, $C_1$-$C_4$ haloalkyl, $C_1$-$C_4$-alkoxy, and $C_1$-$C_4$-haloalkoxy;

$R^x$ is selected from CN, $NO_2$, $C_1$-$C_4$-alkoxy, $C_1$-$C_4$-haloalkoxy, $S(O)_mR^d$, $S(O)_mNR^eR^f$, $C_1$-$C_{10}$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, 5- to 7-membered heterocyclyl, 5- or 6-membered hetaryl, phenyl, $C_3$-$C_6$-cycloalkoxy, 3- to 6-membered heterocyclyloxy, and phenoxy, wherein the last 7 mentioned radicals may be unsubstituted or may carry 1, 2, 3, 4, or 5 radicals $R^y$;

$R^y$ is selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_mR^d$, $S(O)_mNR^eR^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, and $C_1$-$C_4$-alkoxy-$C_1$-$C_4$-alkyl;

and wherein
Y is O or S; and
m is 0, 1 or 2;
and wherein
$X^1$ is a leaving group, which is preferably selected from halogen, $N_3$, p-nitrophenoxy, and pentafluorophenoxy.

In a preferred embodiment,
$R^1$ is $CH_2CH_3$;
$R^2$ is $C_1$-$C_4$-alkyl, which may be unsubstituted, or may be partially or fully halogenated;
$R^3$ is H;
and
$R^N$ is a group —$CR^4R^5R^6$
wherein
  $R^4$ is selected from $C_1$-$C_4$-alkyl, which may be unsubstituted, may be partially or fully halogenated, or may carry 1 or 2 identical or different substituents $R^x$, wherein $R^x$ is selected from CN and $C(O)NH_2$, and
  $C_3$-$C_6$-cycloalkyl, which may be unsubstituted or may carry 1, 2, or 3 identical or different substituents $R^y$, wherein $R^y$ is selected from halogen, CN and $C(O)NH_2$; and
  $R^5$ is selected from $C_1$-$C_4$-alkyl, which may be unsubstituted, may be partially or fully halogenated, or may carry 1 or 2 identical or different substituents $R^x$, wherein $R^x$ is selected from CN and $C(O)NH_2$, and
  $C_3$-$C_6$-cycloalkyl, which may be unsubstituted or may carry 1, 2 or 3 identical or different substituents $R^y$, wherein $R^y$ is selected from halogen, CN and $C(O)NH_2$;
  or
  $R^4$ and $R^5$ together with the carbon atom to which they are attached form a 3- to 12-membered non-aromatic, saturated carbocycle, which may be partially or fully substituted by $R^j$, wherein $R^j$ is selected from halogen, CN, and $C(O)NH_2$; and
  $R^6$ is H;
and
$X^1$ is a leaving group, which is preferably selected from halogen, $N_3$, p-nitrophenoxy, and pentafluorophenoxy, and is particularly preferably chlorine.

In a more preferred embodiment, $R^N$ is —$CR^4R^5R^6$, and
$R^1$ is $CH_2CH_3$; and
$R^2$ is $CH_3$, $R_3$ is H, $R^4$ is $CH_3$, $R^5$ is $CH_3$ and $R^6$ is H; or
$R^2$ is $CH_3$, $R_3$ is H, $R^4$ is $CF_3$, $R^5$ is $CH_3$ and $R^6$ is H; or
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is 1-CN-$cC_3H_4$, $R^5$ is $CH_3$ and $R^6$ is H; or
$R^2$ is $CH_3$, $R_3$ is H, $R^4$ is 1-$C(O)NH_2$-$cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H; and
$X^1$ is a leaving group, which is preferably selected from halogen, $N_3$, p-nitrophenoxy, and pentafluorophenoxy, and is particularly preferably chlorine.

With regard to the reaction conditions for step (v), reference is made to WO 2009/027393 and WO 2010/034737.

In the following, preferred embodiments regarding process B of the invention are provided. It is to be understood that the preferred embodiments mentioned above and those still to be illustrated below of process B of the invention are to be understood as preferred alone or in combination with each other.

As already indicated above, the present invention relates in a second aspect to the process B of preparing (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b)

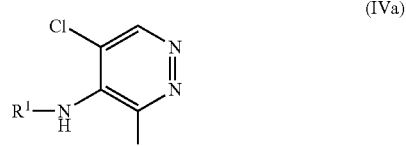

(IVa)

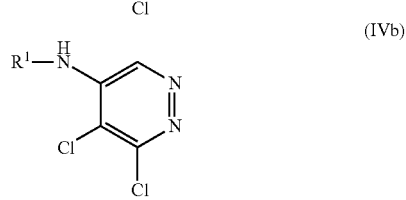

(IVb)

in a one-pot reaction comprising the steps of
reacting a compound of formula II

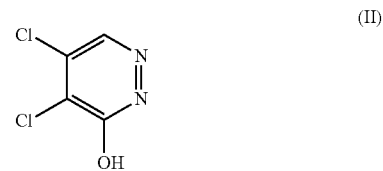

(II)

with $POCl_3$, and
reacting the resulting crude reaction product with an amine compound $R^1$—$NH_2$ or a salt thereof, wherein $R^1$ is H, $C_1$-$C_2$-alkyl, or $C_1$-$C_2$-alkoxy-$C_1$-$C_2$-alkyl.

The reaction step underlying process B corresponds to steps (ii)+(iii) in the above reaction sequence.

As indicated above, the one-pot reaction is advantageous, as the intermediary obtained trichloropyridazine compound of formula III, which is irritating, does not have to be isolated.

As already indicated above, it is to be understood that the compound of formula II may also be present in the form of its pyridazone tautomer.

It is to be understood that (a) or (b) or a mixture of (a) and (b) may be obtained in steps (ii)+(iii).

In a preferred embodiment, a mixture of (a) and (b) is obtained.

The substituent $R^1$ in the compounds of formulae IVa and IVb, and the amine compound $R^1$—$NH_2$ is preferably selected from the group consisting of $CH_3$, $CH_2CH_3$, and $CH_2OCH_3$.

In a preferred embodiment, $R^1$ in the compounds of formulae IVa and IVb, and the amine compound $R^1$—$NH_2$ is $CH_2CH_3$.

In a particularly preferred embodiment, a mixture of (a) and (b) is obtained, and $R^1$ in the compounds of formulae IVa and IVb, and the amine compound $R^1$—$NH_2$ is selected from the group consisting of $CH_3$, $CH_2CH_3$, and $CH_2OCH_3$, and is preferably $CH_2CH_3$.

The reaction conditions for steps (ii) and (iii), which are performed subsequently in the one-pot reaction as defined above, without isolating the intermediary obtained compound of formula III, have already been provided above.

In a preferred embodiment of process B, the process further comprises step (i), i.e. the step of preparing the compound of formula II

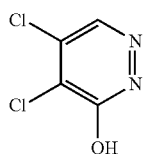
(II)

by reacting mucochloric acid (I)

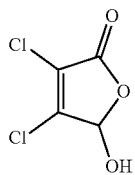
(I)

with hydrazine or a salt thereof.

The reaction conditions for this reaction step (i) have already been provided above.

In another preferred embodiment of process B, the process further comprises step (iv), i.e. the step of converting (a) the dichloropyridazine amine compound of formula IVa or a salt, tautomer, or N-oxide thereof, or (b) the dichloropyridazine amine compound of formula IVb or a salt, tautomer, or N-oxide thereof, or (c) the mixture of (a) and (b) into a pyridazine amine compound of formula V or a salt, tautomer, or N-oxide thereof

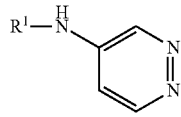
(V)

by reacting (a) the dichloropyridazine amine compound of formula IVa or a salt, tautomer, or N-oxide thereof, or (b) the dichloropyridazine amine compound of formula IVb or a salt, tautomer, or N-oxide thereof, or (c) the mixture of (a) and (b)

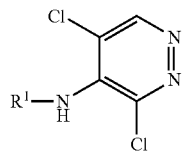
(IVa)

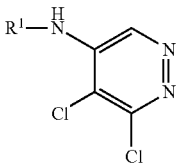
(IVb)

with hydrogen in the presence of a hydrogenation catalyst, wherein $R^1$ is as defined above;

and wherein the process optionally further comprises step (v), i.e. the step of converting the pyridazine amine compound of formula V or a salt, tautomer, or N-oxide thereof into a compound of formula VII or a stereoisomer, salt, tautomer, or N-oxide thereof

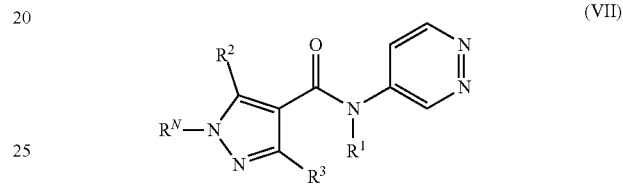
(VII)

by reacting the pyridazine amine compound of formula V or a salt, tautomer, or N-oxide thereof

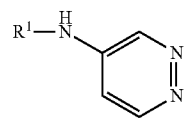
(V)

with a compound of formula VI or a stereoisomer, salt, tautomer, or N-oxide thereof

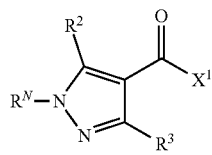
(VI)

wherein $R^1$ is as defined above, and
wherein $R^2$, $R^3$, $R^N$, and $X^1$ are as defined above.

Preferred embodiments and the reaction conditions for the reaction steps (iv) and (v) have already been provided above in connection with process A.

In the following, preferred embodiments regarding process C of the invention are provided. It is to be understood that the preferred embodiments mentioned above and those still to be illustrated below of process C of the invention are to be understood as preferred alone or in combination with each other.

As already indicated above, the present invention relates in a third aspect to the process C of preparing (a) a dichloropyridazine amine compound of formula IVa or a salt, tautomer, or N-oxide thereof, or (b) a dichloropyridazine amine compound of formula IVb or a salt, tautomer, or N-oxide thereof, or (c) a mixture of (a) and (b)

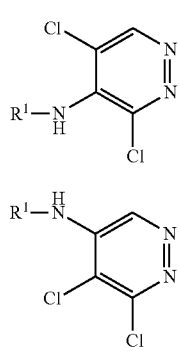

comprising the step of reacting a trichloropyridazine compound of formula III

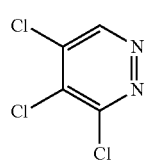

with an amine compound R¹—NH₂ or a salt thereof,
wherein R¹ is CH₂CH₃,
and wherein the process optionally further comprises the step of preparing the trichloropyridazine compound of formula III

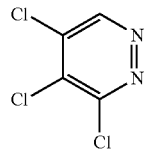

by reacting a compound of formula II

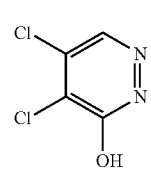

with POCl₃.

The reaction step underlying process C covers step (iii) in the above reaction sequence, and optionally additionally step (ii) as a separate step.

It has surprisingly been found that particularly high yields in the reaction step (iii) can be obtained, if ethylamine is used as the amine compound R¹—NH₂. Furthermore, a laborious work-up is not required.

As already indicated above, it is to be understood that the compound of formula II may also be present in the form of its pyridazone tautomer.

It is to be understood that (a) or (b) or a mixture of (a) and (b) may be obtained in step (iii).

In a preferred embodiment, a mixture of (a) and (b) is obtained.

The reaction conditions for steps (ii) and (iii), which are performed separately according to process C, have already been provided above.

In a preferred embodiment of process C, the process further comprises step (i), i.e. the step of preparing the compound of formula II

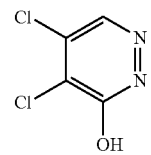

by reacting mucochloric acid (I)

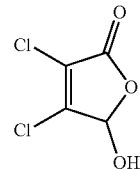

with hydrazine or a salt thereof.

The reaction conditions for this reaction step (i) have already been provided above.

In another preferred embodiment of process C, the process further comprises step (iv), i.e. the step of converting (a) the dichloropyridazine amine compound of formula IVa or a salt, tautomer, or N-oxide thereof, or (b) the dichloropyridazine amine compound of formula IVb or a salt, tautomer, or N-oxide thereof, or (c) the mixture of (a) and (b) into a pyridazine amine compound of formula V or a salt, tautomer, or N-oxide thereof

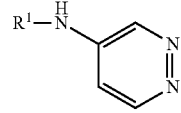

by reacting (a) the dichloropyridazine amine compound of formula IVa or a salt, tautomer, or N-oxide thereof, or (b) the dichloropyridazine amine compound of formula IVb or a salt, tautomer, or N-oxide thereof, or (c) the mixture of (a) and (b)

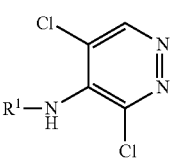

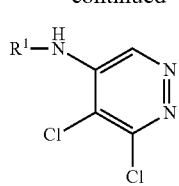

(IVb)

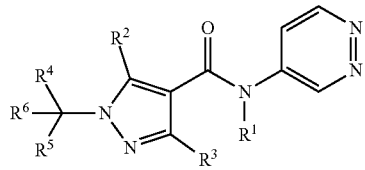

(VII*)

with hydrogen in the presence of a hydrogenation catalyst, wherein $R^1$ is as defined above;

and wherein the process optionally further comprises step (v), i.e. the step of converting the pyridazine amine compound of formula V or a salt, tautomer, or N-oxide thereof into a compound of formula VII or a stereoisomer, salt, tautomer, or N-oxide thereof comprising the step of reacting a pyridazine amine compound of formula V or a salt, tautomer, or N-oxide thereof

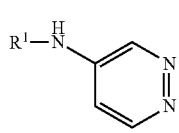

(V)

with a compound of formula VI* or a stereoisomer, salt, tautomer, or N-oxide thereof

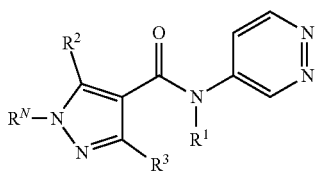

(VII)

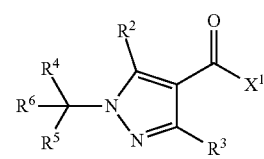

(VI*)

by reacting the pyridazine amine compound of formula V or a salt, tautomer, or N-oxide thereof

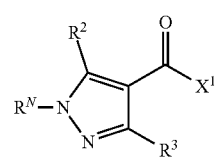

(V)

with a compound of formula VI or a stereoisomer, salt, tautomer, or N-oxide thereof wherein
$R^1$ is $CH_2CH_3$; and wherein
$R^2$ is $CH_3$, $R_3$ is H, $R^4$ is $CH_3$, $R^5$ is $CH_3$ and $R^6$ is H; or
$R^2$ is $CH_3$, $R_3$ is H, $R^4$ is $CF_3$, $R^5$ is $CH_3$ and $R^6$ is H; or
$R^2$ is $CH_3$, $R_3$ is H, $R^4$ is $CH(CH_3)_2$, $R^5$ is $CH_3$ and $R^6$ is H; or
$R^2$ is $CH_3$, $R_3$ is H, $R^4$ is $CHFCH_3$, $R^5$ is $CH_3$ and $R^6$ is H; or
$R^2$ is $CH_3$, $R_3$ is H, $R^4$ is $1\text{-CN-}cC_3H_4$, $R^5$ is $CH_3$ and $R^6$ is H; or
$R^2$ is $CH_3$, $R_3$ is H, $R^4$ is $1\text{-C(O)NH}_2\text{-}cC_3H_4$, $R^5$ is $CH_3$ and $R^6$ is H; or
$R^2$ is $CH_3$, $R_3$ is H, $R^4$ and $R^5$ together are $CH_2CH_2CF_2CH_2CH_2$, and $R^6$ is H;
and wherein
$X^1$ is a leaving group, which is preferably selected from halogen, $N_3$, p-nitrophenoxy, and pentafluorophenoxy, and is particularly preferably chlorine.

(VI)

wherein $R^1$ is as defined above, and
wherein $R^2$, $R^3$, $R^N$, and $X^1$ are as defined above.

Preferred embodiments and the reaction conditions for the reaction steps (iv) and (v) have already been provided above in connection with process A.

In the following, preferred embodiments regarding process D of the invention are provided. It is to be understood that the preferred embodiments mentioned above and those still to be illustrated below of process D of the invention are to be understood as preferred alone or in combination with each other.

As already indicated above, the present invention relates in a further aspect to a process D for the preparation of a compound of formula VII* or a stereoisomer, salt, tautomer, or N-oxide thereof The reaction step underlying process D is covered by step (v) of the above reaction sequence.

In a preferred embodiment, the process further comprises step (iv) of the reaction sequence.

In a more preferred embodiment, the process further comprises step (iii) and optionally also step (ii), wherein steps (ii) and (iii) may be carried out separately via isolation of the compound of formula III, or together in a one-pot reaction.

In an even more preferred embodiment, the process further comprises step (i).

Further details regarding steps (i), (ii), (iii), and (iv) have been provided above.

As already indicated above, the present invention relates in another aspect to a dichloropyridazine amine compound of formula IVa or a salt, tautomer, or N-oxide thereof;

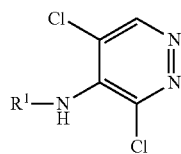

(IVa)

wherein $R^1$ is $CH_2CH_3$;
or a dichloropyridazine amine compound of formula IVb or a salt, tautomer, or N-oxide thereof,

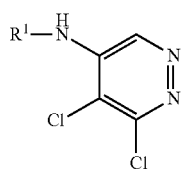

(IVb)

wherein $R^1$ is $CH_2CH_3$.

In a further aspect, the present invention relates to a mixture of the dichloropyridazine amine compound of formula IVa or a salt, tautomer, or N-oxide thereof and the dichloropyridazine amine compound of formula IVb or a salt, tautomer, or N-oxide thereof as defined above, i.e. wherein $R^1$ is in each case $CH_2CH_3$.

These compounds are valuable starting materials for the preparation of 4-ethylaminopyridazine, which itself may, e.g., be converted into pesticididally active 4-pyrazole-N-pyridazineamide compounds of formula VII.

Typically, the mixture of the dichloropyridazine amine compound of formula IVa or a salt, tautomer, or N-oxide thereof and the dichloropyridazine amine compound of formula IVb or a salt, tautomer, or N-oxide thereof as defined above, i.e. wherein $R^1$ is in each case $CH_2CH_3$ may be obtained by processes B or C as described herein. The mixtures may be separated into the components (a) dichloropyridazine amine compound of formula IVa or a salt, tautomer, or N-oxide thereof as and (b) dichloropyridazine amine compound of formula IVb or a salt, tautomer, or N-oxide thereof by separation techniques known to a skilled person, e.g., by column chromatography. However, the separation of the two components is not required for the preparation of the pyridazine amine compound of formula V, as both components are suitable starting materials for the dehalogenation/hydrogenation reaction.

In the mixture, the components (a) dichloropyridazine amine compound of formula IVa or a salt, tautomer, or N-oxide thereof as and (b) dichloropyridazine amine compound of formula IVb or a salt, tautomer, or N-oxide thereof may be present in any ratio, preferably in a weight ratio range of from 100:1 to 1:100, preferably 10:1 to 1:10, more preferably 5:1 to 1:5, most preferably 2:1 to 1:2, particularly preferably 1:1.

EXAMPLES

I. Characterization

The characterization can be done by coupled High Performance Liquid Chromatography/mass spectrometry (HPLC/MS), by NMR or by their melting points.

HPLC: Agilent Extend 1.8 μm C18 4.6×100 mm; mobile phase: A: water+0.1% $H_3PO_4$; B: acetonitrile (MeCN)+ 0.1% $H_3PO_4$; gradient: 5-95% A in 10 minutes; 0-10 minutes is 5:95 A:B then gradient from 10-10.1 minutes to 95:5 A:B flow: 1.2 ml/min in 10 minutes at 60° C.

| min | A | B | Flow | Pressure (bar) |
|---|---|---|---|---|
| 8 | 5 | 95 | 1.2 | 400 |
| 10 | 5 | 95 | 1.2 | 400 |
| 10.1 | 95 | 5 | 1.2 | 400 |

$^1$H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

Abbreviations used are: h for hour(s), min for minute(s) and room temperature for 20-25° C.

II. Preparation Examples

1. Preparation of a mixture of 3,4-dichloro-5-ethylaminopyridazine and 3,5-dichloro-4-ethylaminopyridazine in a one-pot procedure starting from 4,5-dichloro-3-hydroxypyridazine:

200 g of 4,5-dichloro-3-hydroxypyridazine was placed in a reactor at 20° C. under $N_2$, and $POCl_3$ (930 g, 5 equiv) was added and the reaction mixture was heated to 100° C. The reaction mixture was further stirred for ~1 hour until full conversion was achieved. The excess $POCl_3$ was removed via distillation. The reaction mixture was dosed into 1200 g $H_2O$ controlling the temperature at 30° C. Butyl acetate (1200 g) was added and the biphasic mixture was stirred for 30 minutes at 30° C. and then the phases were separated. Another portion of butyl acetate (400 g) was used to wash the aqueous phase. The combined organic phases were washed with 10% HCl and then $H_2O$.

To the mixture of trichloropyridazine in butyl acetate was added a solution of ethylamine in water with a concentration of 70 wt.-% of ethylamine based on the total weight of the solution (234 g, 3 equiv) at 35° C. The reaction was held at 45° C. for 3 hours (or until full conversion is observed). The phases were separated at 40° C. and the organic phase was washed once with $H_2O$. The combined aqueous phases were once extracted with butyl acetate. Butyl acetate from the combined organic phases was distilled (15 mbar, 35° C.) to concentrate the reaction mixture. During this process, the product precipitated from solution. The reaction mixture was cooled to 10° C. and the product was filtered off. The mother liquor was next concentrated and the crude material was recrystallized from MTBE to isolate the remainder of the product.

2. Preparation of 4-ethylaminopyridazine:

600 g (3.09 mol) of a mixture of 3,4-dichloro-5-ethylaminopyridazine and 3,5-dichloro-4-ethylaminopyridazine was dissolved in EtOH (3.5 liters). 15 g (0.01 mol) of 10% Pd/C was added and the pressure reactor was purged with nitrogen. The pressure reactor was pressurized to 0.2 bar with $H_2$ and heated to 35° C. As the reaction is exothermic, the temperature was controlled at 55° C. for 4 hours. Afterwards, the pressure was released and the reactor was purged with $N_2$. The reaction mixture was filtered at room temperature to remove the catalyst. The catalyst can be reused in the next batch without purification.

In a second reactor, a mixture of K₂CO₃ (1 kg) and 1 liter of EtOH was prepared. The reaction mixture was dosed into the potassium carbonate solution over 60 minutes and the temperature was controlled at 20-25° C. The reaction mixture was further stirred for 3 hours. The salts produced in the process were filtered off. A portion of solvent from the reaction mixture was distilled off and MTBE was added to precipitate out the pure ethylaminopyridazine (354 g, 91% purity, 85% yield).

The invention claimed is:

1. A process for preparing at least one of a pyridazine amine compound of formula V, a salt thereof, a tautomer thereof, and an N-oxide thereof

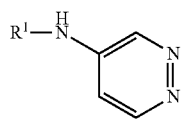
(V)

comprising a step of reacting at least one of (a) at least one of a dichloropyridazine amine compound of formula IVa, a salt thereof, a tautomer thereof, and an N-oxide thereof, (b) at least one of a dichloropyridazine amine compound of formula IVb, a salt thereof, a tautomer thereof, and an N-oxide thereof, and (c) a mixture of (a) and (b)

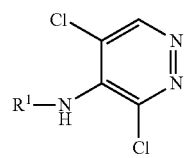
(IVa)

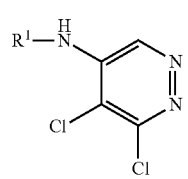
(IVb)

with hydrogen in the presence of a hydrogenation catalyst, wherein the process further comprises the step of preparing the at least one of (a) the at least one of the dichloropyridazine amine compound of formula IVa, the salt thereof, the tautomer thereof, and the N-oxide thereof, and (b) the at least one of the dichloropyridazine amine compound of formula IVb, the salt thereof, the tautomer thereof, and the N-oxide thereof, and (c) the mixture of (a) and (b) in a one-pot reaction comprising the steps of:

reacting a compound of formula (II)

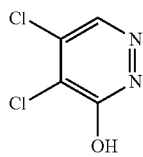
(II)

with POCl₃, and reacting a resulting crude reaction product with at least one of an amine compound R¹—NH₂ or a salt thereof;

and wherein said reaction between the resulting crude reaction product and the amine compound R¹—NH₂, or a salt thereof, is carried out at temperatures in a range of from 30° C. to 50° C.;

R¹ of formulas V, IVa, and IVb is selected from the group consisting of H, and C₁-C₂-alkoxy-C₁-C₂-alkyl.

2. The process according to claim 1, wherein the step of reacting is performed in the absence of a HCl scavenger.

3. The process according to claim 2, wherein a HCl scavenger is added after removal of the hydrogenation catalyst, and wherein the HCl scavenger is provided without water.

4. The process according to claim 3, wherein the HCl scavenger is selected from the group consisting of bases including alkali metal and alkaline earth metal hydroxides, alkali metal and alkaline earth metal oxides, alkali metal and alkaline earth metal hydrides, alkali metal amides, alkali metal and alkaline earth metal carbonates, alkali metal bicarbonates, alkali metal alkyls, alkylmagnesium halides, alkali metal and alkaline earth metal alcoholates, nitrogen-containing bases including tertiary amines, pyridines, bicyclic amines, ammonia, and primary amines, and combinations thereof; buffers including at least one of sodium acetate and ammonium formate; precursors of ionic liquids including imidazoles; and combinations thereof.

5. The process according to claim 1, wherein the hydrogenation catalyst is selected from the group consisting of platinum on a carrier, palladium on a carrier, Raney nickel, and Raney cobalt.

6. The process according to claim 1, wherein R¹ of formulas V, IVa, and IVb is CH₂CH₃.

7. The process according to claim 1, wherein the process further comprises a step of preparing a compound of formula II

(II)

by reacting mucochloric acid (I)

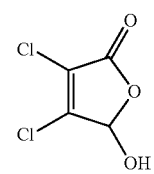
(I)

with at least one of hydrazine and a salt thereof.

8. A process for preparing a compound of formula VII or a stereoisomer, salt, tautomer, or N-oxide thereof

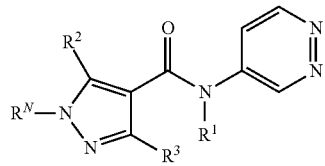

comprising a step of reacting at least one of (a) at least one of a dichloropyridazine amine compound of formula IVa, a salt thereof, a tautomer thereof, and an N-oxide thereof, (b) at least one of a dichloropyridazine amine compound of formula IVb, a salt thereof, a tautomer thereof, and an N-oxide thereof, and (c) a mixture of (a) and (b)

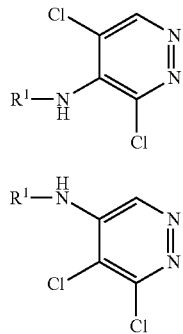

with hydrogen in the presence of a hydrogenation catalyst, to afford a pyridazine amine compound of formula V, a salt, a tautomer, or an N-oxide thereof;

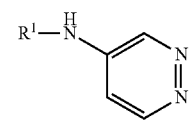

wherein the process further comprises the step of preparing the at least one of (a) the at least one of the dichloropyridazine amine compound of formula IVa, the salt thereof, the tautomer thereof, and the N-oxide thereof, and (b) the at least one of the dichloropyridazine amine compound of formula IVb, the salt thereof, the tautomer thereof, and the N-oxide thereof, and (c) the mixture of (a) and (b) in a one-pot reaction comprising the steps of:
reacting a compound of formula (II)

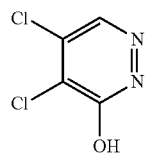

with $POCl_3$, and
reacting a resulting crude reaction product with at least one of an amine compound $R^1-NH_2$ or a salt thereof;
and wherein said reaction between the resulting crude reaction product and the amine compound $R^1-NH_2$, or a salt thereof, is carried out at temperatures in a range of from 30° C. to 50° C.;
$R^1$ of formulas V, IVa, and IVb is selected from the group consisting of H, and $C_1$-$C_2$-alkoxy-$C_1$-$C_2$-alkyl;
reacting the pyridazine amine compound of formula V or a salt, tautomer, or N-oxide thereof;
with a compound of formula VI or a stereoisomer, salt, tautomer, or N-oxide thereof

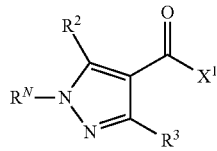

to afford the compound of formula (VII);
and wherein
$R^2$ is H, halogen, CN, $NO_2$, $C_1$-$C_{10}$-alkyl, $C_2$-$C_{10}$-alkenyl, or $C_2$-$C_{10}$-alkynyl, wherein the 3 last mentioned radicals may be unsubstituted, may be partially or fully halogenated or may carry 1, 2 or 3 identical or different substituents $R^x$, or
$OR^a$, $SR^a$, $C(Y)R^b$, $C(Y)OR^c$, $S(O)R^d$, $S(O)_2R^d$, $NR^eR^f$, $C(Y)NR^gR^h$, heterocyclyl, hetaryl, $C_3$-$C_{10}$-cycloalkyl, $C_3$-$C_{10}$-cycloalkenyl or phenyl, wherein the five last mentioned radicals may be unsubstituted or may carry 1, 2, 3, 4 or 5 identical or different substituents selected from the radicals $R^y$ and $R^x$;
$R^3$ is H, halogen, CN, $NO_2$, $C_1$-$C_{10}$-alkyl, $C_2$-$C_{10}$-alkenyl, or $C_2$-$C_{10}$-alkynyl, wherein the 3 last mentioned radicals may be unsubstituted, may be partially or fully halogenated or may carry 1, 2 or 3 identical or different substituents $R^x$, or
$OR^a$, $SR^a$, $C(Y)R^b$, $C(Y)OR^c$, $S(O)R^d$, $S(O)_2R^d$, $NR^eR^f$, $C(Y)NR^gR^h$, heterocyclyl, hetaryl, $C_3$-$C_{10}$-cycloalkyl, $C_3$-$C_{10}$-cycloalkenyl or phenyl, wherein the five last mentioned radicals may be unsubstituted or may carry 1, 2, 3, 4 or 5 identical or different substituents selected from the radicals $R^y$ and $R^x$;
$R^N$ is H, CN, $NO_2$, $C_1$-$C_{10}$-alkyl, $C_2$-$C_{10}$-alkenyl, or $C_2$-$C_{10}$-alkynyl, wherein the three last mentioned radicals may be unsubstituted, may be partially or fully halogenated or may carry 1, 2 or 3 identical or different substituents $R^x$, or
$OR^a$, $SR^a$, $C(Y)R^b$, $C(Y)OR^c$, $S(O)R^d$, $S(O)_2R^d$, $NR^eR^f$, $C(Y)NR^gR^h$, $S(O)_mNR^eR^f$, $C(Y)NR^iNR^eR^f$, $C_1$-$C_5$-alkylen-$OR^a$, $C_1$-$C_5$-alkylen-CN, $C_1$-$C_5$-alkylen-$C(Y)R^b$, $C_1$-$C_5$-alkylen-$C(Y)OR^c$, $C_1$-$C_5$-alkylen-$NR^eR^f$, $C_1$-$C_5$-alkylen-$C(Y)NR^gR^h$, $C_1$-$C_5$-alkylen-$S(O)_mR^d$, $C_1$-$C_5$-alkylen-$S(O)_mNR^eR^f$, $C_1$-$C_5$-alkylen-$NR^iN$-$R^eR^f$, heterocyclyl, hetaryl, $C_3$-$C_{10}$-cycloalkyl, $C_3$-$C_{10}$-cycloalkenyl, heterocyclyl-$C_1$-$C_5$-alkyl, hetaryl-$C_1$-$C_5$-alkyl, $C_3$-$C_{10}$-cycloalkyl-$C_1$-$C_5$-alkyl, $C_3$-$C_{10}$-cycloalkenyl-$C_1$-$C_5$-alkyl, phenyl-$C_1$-$C_5$-alkyl, or phenyl, wherein the rings of the ten last mentioned radicals may be unsubstituted or may carry 1, 2, 3, 4 or 5 identical or different substituents BY;

and wherein $R^a$, $R^b$, $R^c$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl, and hetaryl-$C_1$-$C_4$-alkyl, wherein the ring in the six last mentioned radicals may be unsubstituted or may carry 1, 2, 3, 4, or 5 substituents which, independently of each other, are selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^d$ is selected from $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl, and hetaryl-$C_1$-$C_4$-alkyl, wherein the ring in the six last mentioned radicals may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^e$, $R^f$ are independently of each other selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, $C_1$-$C_4$-alkylcarbonyl, $C_1$-$C_4$-haloalkylcarbonyl, $C_1$-$C_4$-alkyl sulfonyl, $C_1$-$C_4$-haloalkylsulfonyl, heterocyclyl, heterocyclyl-$C_1$-$C_4$-alkyl, heterocyclylcarbonyl, heterocyclylsulfonyl, phenyl, phenylcarbonyl, phenyl sulfonyl, hetaryl, hetarylcarbonyl, hetarylsulfonyl, phenyl-$C_1$-$C_4$-alkyl, and hetaryl-$C_1$-$C_4$-alkyl, wherein the ring in the twelve last mentioned radicals may be unsubstituted or may carry 1, 2, 3, 4, or 5 substituents which, independently of each other, are selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy; or $R^e$ and $R^f$ together with the nitrogen atom to which they are bound form a 5- or 6-membered, saturated or unsaturated heterocycle, which may carry a further heteroatom being selected from O, S and N as a ring member atom and wherein the heterocycle may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^g$, $R^h$ are independently of each other selected from H, $C_1$-$C_4$-alkyl, $C_1$-$C_4$-haloalkyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, heterocyclyl, heterocyclyl-$C_1$-$C_4$-alkyl, phenyl, hetaryl, phenyl-$C_1$-$C_4$-alkyl, and hetaryl-$C_1$-$C_4$-alkyl, wherein the ring in the six last mentioned radicals may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^i$ is selected from H, $C_1$-$C_4$-alkyl, $C_1$-$C_4$-haloalkyl, $C_3$-$C_6$-cycloalkyl, $C_3$-$C_6$-cycloalkylmethyl, $C_3$-$C_6$-halocycloalkyl, $C_2$-$C_4$-alkenyl, $C_2$-$C_4$-haloalkenyl, $C_2$-$C_4$-alkynyl, $C_1$-$C_4$-alkoxy-$C_1$-$C_4$-alkyl, phenyl, and phenyl-$C_1$-$C_4$-alkyl, wherein the phenyl ring in the two last mentioned radicals may be unsubstituted or may carry 1, 2, 3, 4, or 5 substituents which are independently of each other selected from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

$R^x$ is selected from CN, $NO_2$, $C_1$-$C_4$-alkoxy, $C_1$-$C_4$-haloalkoxy, $S(O)_m R^d$, $S(O)_m NR^e R^f$, $C_1$-$C_{10}$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, 5- to 7-membered heterocyclyl, 5- or 6-membered hetaryl, phenyl, $C_3$-$C_6$-cycloalkoxy, 3- to 6-membered heterocyclyloxy, and phenoxy, wherein the last 7 mentioned radicals may be unsubstituted or may carry 1, 2, 3, 4, or 5 radicals $R^y$;

$R^y$ is selected from halogen, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_m R^d$, $S(O)_m NR^e R^f$, $C_1$-$C_4$-alkylcarbonyl, $C_1$-$C_4$-haloalkylcarbonyl, $C_1$-$C_4$-alkoxycarbonyl, $C_1$-$C_4$-haloalkoxycarbonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl, and $C_1$-$C_4$-alkoxy-$C_1$-$C_4$-alkyl;

and wherein

Y is O or S; and m is 0, 1 or 2;

and wherein $X^1$ is selected from halogen, $N_3$, p-nitrophenoxy, and pentafluorophenoxy.

9. The process according to claim 8, wherein $R^1$ is $CH_2CH_3$;

$R^2$ is $C_1$-$C_4$-alkyl, which may be unsubstituted, or may be partially or fully halogenated;

$R^3$ is H;

and wherein $R^N$ is a group —$CR^4R^5R^6$ wherein $R^4$ is selected from $C_1$-$C_4$-alkyl, which may be unsubstituted, may be partially or fully halogenated, or may carry 1 or 2 identical or different substituents $R^x$, wherein $R^x$ is selected from CN and $C(O)NH_2$, and $C_3$-$C_6$-cycloalkyl, which may be unsubstituted or may carry 1, 2, or 3 identical or different substituents $R^y$, wherein $R^y$ is selected from halogen, CN and $C(O)NH_2$; and $R^5$ is selected from $C_1$-$C_4$-alkyl, which may be unsubstituted, may be partially or fully halogenated, or may carry 1 or 2 identical or different substituents $R^x$, wherein $R^x$ is selected from CN and $C(O)NH_2$, and $C_3$-$C_6$-cycloalkyl, which may be unsubstituted or may carry 1, 2 or 3 identical or different substituents $R^y$, wherein $R^y$ is selected from halogen, CN and $C(O)NH_2$;

or $R^4$ and $R^5$ together with the carbon atom to which they are attached form a 3- to 12-membered non-aromatic, saturated carbocycle, which may be partially or fully substituted by $R^j$, wherein $R^j$ is selected from halogen, CN, and $C(O)NH_2$; and $R^6$ is H;

and wherein $X^i$ is selected from halogen, $N_3$, p-nitrophenoxy, and pentafluorophenoxy.

10. A process for preparing at least one of (a) at least one of a dichloropyridazine amine compound of formula IVa, a salt thereof, a tautomer thereof, and an N-oxide thereof, (b) a dichloropyridazine amine compound of formula IVb, a salt thereof, a tautomer thereof, and an N-oxide thereof, and (c) a mixture of (a) and (b)

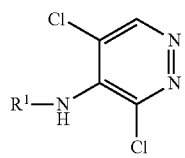

(IVa)

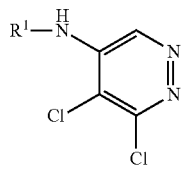

(IVb)

in a one-pot reaction comprising steps of:
reacting a compound of formula II

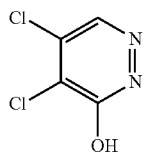

(II)

with POCl$_3$, and reacting the resulting crude reaction product with at least one of an amine compound R$^1$—NH$_2$ a salt thereof, wherein R$^1$ of formulas IVa and IVb is selected from the group consisting of H, C$_1$-C$_2$-alkyl, and C$_1$-C$_2$-alkoxy-C$_1$-C$_2$-alkyl, wherein said reaction between the resulting crude reaction product and the amine compound R$^1$—NH$_2$, or a salt thereof, is carried out at temperatures in a range of from 30° C. to 50° C.

11. The process according to claim 10, wherein the process further comprises the step of preparing a compound of formula II

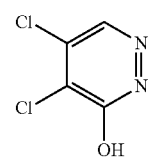

(II)

by reacting mucochloric acid (I)

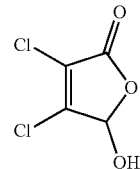

(I)

with at least one of a hydrazine and a salt thereof.

* * * * *

UNITED STATES PATENT AND TRADEMARK OFFICE
CERTIFICATE OF CORRECTION

PATENT NO. : 10,584,102 B2
APPLICATION NO. : 15/572303
DATED : March 10, 2020
INVENTOR(S) : Eric George Klauber et al.

It is certified that error appears in the above-identified patent and that said Letters Patent is hereby corrected as shown below:

In the Claims

At Column 40, Line 11, "H," should be -- H, $C_1$-$C_2$-alkyl, --.

At Column 42, Line 9, "H," should be -- H, $C_1$-$C_2$-alkyl, --.

At Column 42, Line 67, "BY;" should be -- $R^y$; --.

At Column 43, Line 30, "$C_1$-$C_4$-alkyl sulfonyl," should be -- $C_1$-$C_4$-alkylsulfonyl, --.

At Column 43, Line 33, "phenyl sulfonyl," should be -- phenylsulfonyl, --.

At Column 44, Line 60, "$X^i$" should be -- $X^1$ --.

Signed and Sealed this
Twenty-third Day of April, 2024

Katherine Kelly Vidal
*Director of the United States Patent and Trademark Office*